United States Patent
Ogbonna et al.

(10) Patent No.: US 10,775,371 B2
(45) Date of Patent: Sep. 15, 2020

(54) METHODS FOR DETECTING ANALYTES

(71) Applicant: ORTHO-CLINICAL DIAGNOSTICS, INC., Raritan, NJ (US)

(72) Inventors: Godwin Ogbonna, Pittsford, NY (US); Shari Jackson, Rochester, NY (US); Timothy Mangan, Honeoye Falls, NY (US); Jody Parsells, Farmington, NY (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 376 days.

(21) Appl. No.: 15/910,053

(22) Filed: Mar. 2, 2018

(65) Prior Publication Data

US 2018/0259509 A1    Sep. 13, 2018

Related U.S. Application Data

(60) Provisional application No. 62/468,114, filed on Mar. 7, 2017.

(51) Int. Cl.
| | |
|---|---|
| *G01N 33/53* | (2006.01) |
| *G01N 33/543* | (2006.01) |
| *G01N 33/68* | (2006.01) |
| *C07K 16/18* | (2006.01) |
| *C07K 16/30* | (2006.01) |

(52) U.S. Cl.
CPC ....... *G01N 33/54366* (2013.01); *C07K 16/18* (2013.01); *C07K 16/3015* (2013.01); *G01N 33/54313* (2013.01); *G01N 33/54393* (2013.01); *G01N 33/6893* (2013.01); *G01N 2333/4745* (2013.01); *G01N 2333/8146* (2013.01)

(58) Field of Classification Search
None
See application file for complete search history.

(56) References Cited

U.S. PATENT DOCUMENTS

| | | |
|---|---|---|
| 5,656,049 A | 7/1997 | Tayi |
| 5,705,357 A | 4/1998 | Kissel et al. |
| 6,663,833 B1 | 12/2003 | Stave et al. |
| 2003/0113713 A1* | 6/2003 | Glezer .............. G01N 33/5438 435/5 |
| 2004/0093983 A1 | 5/2004 | Mishima et al. |
| 2006/0223193 A1 | 10/2006 | Song et al. |
| 2012/0178186 A1* | 7/2012 | Nieuwennhuis ........................... G01N 33/54326 436/501 |

OTHER PUBLICATIONS

Search Report and Written Opinion issued in related International Patent Application No. PCT/US2018/020554 dated May 17, 2018.

* cited by examiner

*Primary Examiner* — Gary Counts
(74) *Attorney, Agent, or Firm* — K&L Gates LLP; Louis C. Cullman; Brian J. Novak

(57) ABSTRACT

The present disclosure provides methods for the detection of multiple analytes using a single solid phase. The present disclosure also relates to the preparation of solid phases that include receptacles having affixed thereto antibodies directed to at least two different analytes. The methods of the present disclosure can be used, for example, for the quantitative detection of analytes in a sample and the measurement thereof.

26 Claims, 3 Drawing Sheets

METHODS FOR DETECTING ANALYTES

CROSS REFERENCE TO RELATED APPLICATION

This application claims the benefit of priority from U.S. Provisional Application No. 62/468,114, filed on Mar. 7, 2017, the entire content of which is incorporated herein by reference.

FIELD OF THE DISCLOSURE

The present disclosure relates to methods for the detection and measurement of analytes in a sample. The present disclosure also relates to the preparation of a solid phase that includes receptacles with antibodies immobilized thereto that are directed to at least two different analytes. The methods of the present disclosure can be used, for example, for the detection of analytes in a sample and the measurement thereof.

BACKGROUND

Current quantitative methods and assays, such as immunoassays, for determining the presence and amount of specific analytes in a sample are limited to the recognition of a single antigen (analyte) per solid phase. Generally, such quantitative methods are limited to the use of a solid phase, such as a plate containing microwells or a membrane that have only one specific antibody immobilized thereto. See US 2016/0289308; US 2016/0297893. Typically, the antibodies used in such assays are labeled (e.g., fluorescent, radioactive, luminescent, secondary antibody) in a manner that renders them detectable (or not) once they bind an antigen in the sample. Hence, in order to quantitatively detect more than one analyte in a sample, assays currently employ the use of separate solid phase components each having a single antibody specific for one particular analyte immobilized thereto.

Previous attempts to utilize a single solid phase to detect multiple analytes have been directed to the use of lateral flow assays (see, e.g., US 2016/0289308; US 2016/0297893; and US 2010/061377). Lateral flow assays require a test sample to flow in a chromatographic fashion along a bibulous or non-bibulous porous solid phase, such as a membrane. In a typical, lateral flow assay a sample is applied to the solid phase at a first location (i.e., an application zone) and transits the solid phase until the sample reaches a second discrete location (a first test zone) on the solid phase, which includes a first antibody specific to a first analyte. The first test zone is then analyzed to determine the presence or amount of a first analyte in the sample. The sample then must flow until it reaches a third discrete location (second test zone) on the solid phase, which includes another antibody that is specific to another analyte. In a lateral flow assay, the second test zone is then analyzed to determine the presence or amount of analyte in the sample. Determination of the presence of analytes in a lateral flow assay requires a detectable signal at each discrete location (test zone) on the solid phase, which is then read by an instrument such as a fluorometer. However, in order to decipher the amount of each analyte detected in each zone distinct labels are typically used, such as different wavelengths of light, different fluorescent dye labels or different labeled secondary antibodies. As such, lateral flow detection assays are expensive, technically complex and prone to operator based errors.

Solid phase analyte immunoassays are often able to "detect" the presence of multiple analytes in a sample but only in a qualitative fashion. In some instances, solid phase analyte immunoassays include a solid phase having multiple analytes immobilized thereto can be quantitative, but these are limited to competitive assays. For example, in solid phase analyte immunoassays, analytes not antibodies are bound to a solid phase. The bound analytes compete with analyte present in a sample for binding to a labeled antibody specific for the analyte of interest. In these assays, the sample (and antibody bound thereto) is removed in a wash step resulting in a loss of signal compared to that of a solid phase that containing immobilized analytes that are all bound to a detectable antibody (i.e., a control). Hence, the presence of an analyte in a sample is deduced from a reduction signal when compared to a control. As stated above, detection of multiple analytes using a single solid phase requires differentially labeled antibodies and requires the application and reapplication of a sample and specific antibodies to the solid phase. The application of multiple labeled antibodies and subsequent wash steps that are required by such applications make the competitive solid phase assays inefficient, labor intensive and costly. Additionally, competitive assays are susceptible to the non-complexed labeled antibodies binding to "immunoreactive" polypeptide species present in the sample instead of the analyte of interest, and thus prone to false positives.

Solid phase immunoassays for the detection of multiple analytes through the use of a solid phase with multiple antibodies attached thereto are generally qualitative. For example, when a sample is provided to a solid phase that incorporates a plurality of antibodies, each of which is specific to a different antigen of interest is contacted with a sample; if the sample contains any of the antigens of interest a signal would be produced. However, the assay is incapable of deciphering between which of the numerous antigens of interest are present in the sample, without different distinct labels and means for detecting each distinct label. Further, the signal obtained in such assays is a composite of the signals produced by all the different bound antigens. Hence, current methods are incapable of quantitatively determining how much of a specific antigen of interest is present in a sample without using a separate solid phase for each analyte of interest.

In view of the foregoing, the requirements for producing separate solid phase components specific to each analyte assayed renders multi-analyte assays imprecise, expensive, technically complex, and time-consuming. Therefore, a need exists for methods that enable the quantitative detection of multiple analytes in a sample using a single solid phase.

SUMMARY OF THE DISCLOSURE

The methods provided herein utilize a single solid phase that includes a plurality of receptacles. Each receptacle has at least two antibodies (capture antibodies) affixed thereto. Each capture antibody recognizes an antigen (analyte), and the at least two capture antibodies recognize at least two different antigens (analytes) of interest. Therefore, the methods provided herein facilitate the detection of multiple analytes using a single solid phase. The use of a single solid phase to detect multiple analytes eliminates costs associated with producing a separate solid phase for the detection of each specific analyte of interest. The use of a single solid phase to detect multiple analytes in a sample also requires fewer consumables (e.g., reagents and buffers) and allows for more efficient use of internal space within automated assay instruments. The methods of the present disclosure also improve efficiency by limiting the potential for user error by simplifying known experimental procedures and reducing the amount of components necessary to detect multiple analytes in a sample. In addition, the present methods utilize labeled detection antibodies having the same detectable label. This further simplifies the detection of multiple analytes by reducing the need for differentially detectable labels, and means for quantitatively detecting multiple signals.

In a first aspect, the present disclosure provides a method for detecting the presence of analytes of interest in a sample. The method includes providing a solid phase that includes receptacles that are each coated with antibodies that bind (capture) at least two different analytes of interest in a sample, if present. Each receptacle includes two or more different capture antibodies immobilized to a surface thereof, whereby at least two of the immobilized antibodies each recognize a different analyte (i.e., the at least two of the immobilized antibodies recognize at least two different analytes).

In some embodiments, an analyte is any polypeptide that includes an epitope or amino acid sequence of interest. In certain embodiments, polypeptide (protein) analytes can be isolated from cells, synthetically produced, or recombinantly produced. In one embodiment, an analyte is a protein or a fragment thereof that has been produced by a cell. In certain embodiments, the analyte is a protein that is present on the outermost surface of the cellular membrane. In one embodiment, the protein present on the outermost surface of the cellular membrane has an antigen or epitope that is accessible to an antibody. In yet other embodiments, an analyte is a protein or a fragment thereof that has been secreted by a cell.

In certain exemplary embodiments, an analyte is insulin-like growth factor-binding protein 7 (IGFBP7), a derivative, analog or homolog thereof. In other exemplary embodiments, an analyte is an inhibitor of matrix metalloproteinase, a derivative, analog or homolog thereof. In certain embodiments, the analyte is a tissue-inhibitor of metalloproteinase (TIMP).

In some embodiments, analytes in the present disclosure include at least 2, at least 3, at least 4, at least 5, at least 6 or more different proteins or polypeptides. In specific embodiments, the analytes in the present disclosure include two different polypeptides or proteins. In one embodiment, the methods of the present disclosure are employed to detect the presence and/or amount of TIMP2 and IGFP7 in a sample.

In some embodiments, the antibodies immobilized to a receptacle of a solid phase recognize at least two different antigens or epitopes (analytes). In certain embodiments of the present methods, a solid phase receptacle includes 2, 3, 4, 5, 6, 7, 8, 9, 10, or more different antibodies immobilized to a surface thereof. In specific embodiments, the capture antibodies bind two different analytes of interest. In another embodiment, the capture antibodies immobilized to each receptacle of a solid phase are specific to TIMP2 and IGFP7. In some embodiment, the antibodies are monoclonal antibodies specific to TIMP2 and IGFBP7. In certain embodiments, the capture antibodies immobilized to each receptacle of a solid phase are mouse monoclonal antibodies specific to TIMP2 and IGFBP7. In a specific embodiment, the capture antibody specific to TIMP2 is mouse monoclonal antibody 6E2.1 and the capture antibody specific to IGFBP7 is mouse monoclonal antibody 1D6.

In certain embodiments, capture antibodies can be either directly or indirectly affixed to a surface of a receptacle. For example, a capture antibody can be directly covalently bound to a solid phase through a chemical bond between a portion of the capture antibody and a functional group on a surface of the solid phase. Alternatively, a capture antibody can be indirectly covalently bound to a solid phase by covalently binding the antibody to a linker and binding the linker to the solid phase. In some embodiments, a capture antibody is directly non-covalently bound to a solid phase through non-covalent association or adsorption of the antibody to the receptacles.

In some embodiments, the surface of receptacle of a solid phase can be coated to facilitate attachment of a capture antibody. In other embodiments, the receptacle includes functional groups that are incorporated into the material of the receptacle. In certain embodiments, the surface of a receptacle is coated with avidin and the capture antibodies are conjugated to biotin, or vice versa. In one embodiment, capture antibodies are immobilized to a receptacle surface by adsorption after coating with polystyrene.

In some embodiments, the solid phase used in the present methods is composed of polystyrene. In certain embodiments, the receptacles of a solid phase are composed of polystyrene. In a specific embodiment, the receptacles of a solid phase are composed of white polystyrene.

A solid phase can take a variety of forms, which can include, for example, a membrane; a chip; a straw; a sleeve; a slide; a column; a hollow, solid, semi-solid; a gel; a fiber, and a matrix.

In some embodiments, the solid phase includes two or more receptacles in a sealed straw or sleeve. Non-limiting examples of receptacles include cups, wells, tubes, capillaries, vials and any other vessel, groove or indentation capable of holding a solution, a sample or a portion thereof. A receptacle can be contained in a solid phase, such as part of a straw, sleeve, a strip, a plate, a slide, or the like that includes at least two receptacles. In some embodiments, the solid phase includes two or more receptacles in a sealed straw or sleeve. In one embodiment, a solid phase for use in the present methods includes receptacles with vertical sidewalls that are tapered from top to bottom, such that the bottom portion of the receptacle has a width that is less than the width of the upper portion of the receptacle.

In some embodiments of the present methods, a solid phase includes a plurality of receptacles. In certain embodiments, the solid phase includes at least 2 receptacles, at least 3 receptacles, at least 4 receptacles, at least 5 receptacles, at least 6 receptacles, at least 7 receptacles, at least 8 receptacles, at least 9 receptacles, at least 10 receptacles, at least 15 receptacles, at least 20 receptacles, at least 25 receptacles or more. In an embodiment, a solid phase used in the present methods includes at least 2 receptacles. In other embodiments, the solid phase includes at least 2 tapered receptacles.

The methods further include providing a sample or a portion thereof to each receptacle, such that the sample comes in contact with the capture antibodies immobilized to each receptacle. When the sample contains an analyte (e.g., a protein of interest or fragment thereof) recognized by an immobilized capture antibody, the analyte in the sample binds to the specific antibody present in the receptacle.

In certain embodiments, a sample may be obtained from a subject, or may be obtained from other materials. In some instances, the sample is created for the purpose of determining the presence of certain analytes therein. In specific embodiments, samples for use in the present methods are body fluid samples obtained from a subject, such as a patient. In some embodiments, samples of the present disclosure include blood, tears, serum, plasma, cerebrospinal fluid, urine, saliva, sputum, and pleural effusions. In a specific embodiment, the sample is a urine sample obtained from a subject, such as a human. In some instances, the present methods will use multiple portions of a single sample.

In certain embodiments, the sample is urine and the amount of urine provided to each receptacle is from 5 µL to 100 µL, 10 µL to 100 µL, 20 µL to 100 µL, 30 µL to 100 µL, or 40 µL to 100 µL. In other embodiments, the amount of urine provided to each receptacle is from 20 µL to 80 µL, 25 µL to 80 µL, 30 µL to 80 µL, 35 µL to 80 µL, or 40 µL to 80 µL. In yet other embodiments, the amount of urine sample provided to each receptacle is about 20 µL, 25 µL, 30 µL, 35 µL 40 µL, 45 µL, 50 µL, 55 µL, 60 µL, 65 µL, 70 µL, 75 µL, 80 µL or more. In some embodiments, the amount of urine sample provided to each receptacle is exactly 20 µL, 25 µL, 30 µL, 35 µL, 40 µL, 45 µL, 50 µL, 55 µL, 60 µL, 65 µL, 70 µL, 75 µL or 80 µL. In a specific embodiment, the amount of urine sample provided to each receptacle is 20 µL or 35 µL. In one embodiment, the amount of urine sample provided to each receptacle is 80 µL.

Administration of a sample or a portion thereof to a receptacle can be carried out by an individual or an automated device, such as an automated immunodiagnostic device. In embodiments where the present methods are carried out, in-whole or in-part, by an automated immunodiagnostic device, the sample is first provided to a designated reservoir and a portion of the sample is subsequently dispensed to a receptacle or multiple receptacles of a solid phase, which have been provided to the automated immunodiagnostic device. In one embodiment, the methods of the present disclosure are carried out in one of the following automated immunodiagnostic devices Ortho Clinical Diagnostics VITROS® ECiQ, Ortho Clinical Diagnostics VITROS® 3600 or Ortho Clinical Diagnostics VITROS® 5600.

In some embodiments, the sample is provided to each receptacle and incubated for a period of time to facilitate the binding of any analytes of interest present in the sample to a corresponding capture antibody present on each receptacle of the solid phase.

The methods of the present disclosure also include providing an antibody that includes a detectable element (detection antibody) to each receptacle. The detection antibody provided to each receptacle is specific to one of the analytes of interest. More specifically, the present methods include providing an amount of a detection antibody that recognizes a first analyte of interest to a first receptacle of a solid phase, and separately providing an amount of another detection antibody that recognizes a different analyte of interest to another receptacle of the solid phase. The detection antibodies provided to each well all produce the same detectable signal. This aspect of the present methods simplifies the detection of multiple analytes by reducing the need for a user to obtain detection antibodies with differentially detectable labels, as well as means for detecting multiple different signals.

In some embodiments of the present methods, the detection antibodies are monoclonal antibodies, polyclonal antibodies, fragments thereof or any combination thereof. In specific embodiments, the detection antibodies of the present disclosure are all monoclonal antibodies, which each recognize a different analyte of interest. In other embodiments, the detection antibodies of the present disclosure are all polyclonal antibodies, which each recognize a different analyte of interest. In yet another embodiment, the detection antibodies of the present disclosure are a combination of monoclonal antibodies and polyclonal antibodies, each of which is specific to a different analyte of interest.

In some embodiments of the present methods, the detection antibodies are specific to TIMP2 and IGFP7, respectively. In certain embodiments, the detection antibodies of the present disclosure are monoclonal antibodies specific to TIMP2 and IGFBP7, respectively. In specific embodiments, the detection antibody that is specific to TIMP2 is rabbit monoclonal antibody 40H2-40K3, and the detection antibody that is specific to IGFBP7 is mouse monoclonal antibody 6D2.1.

In one embodiment, the detectable label associated with a detection antibody is directly detectable. In certain embodiments, the directly detectable label is a fluorescent moiety (dye), an electrochemical label, an electrochemical luminescence label, metal chelates, or a colloidal metal particle.

In other embodiments, the detectable label is an indirectly detectable label, such as a molecule that is detectable after it is subjected to a chemical or enzymatic reaction, or bound by a molecule that itself provides a detectable signal. In some embodiments, the detectable label is an enzyme, such as horseradish peroxidase (HRP) or alkaline phosphatase.

In some embodiments, a detectable label is attached to a detection antibody. In specific embodiments, the detectable label is conjugated to the detection antibody. In certain embodiments, the detectable label is a dye or enzyme that is conjugated to each detection antibody. In one embodiment of the present methods, horseradish peroxidase is used as a conjugate with each specific detection antibody.

A detection antibody may be dispensed directly into a receptacle or pre-mixed in a solution that includes a desired concentration of detection antibody and provided as an aliquot of such pre-mixed solution.

In some embodiments, the amount of detection antibody provided to each receptacle is from about 0.02 µg to about 1.2 µg. In one embodiment, amount of detection antibody provided to each receptacle is from 0.02 µg to 1.2 µg. In a specific embodiment, the amount of detection antibody provided to each receptacle is 0.075 µg or 1.2 µg.

Administration of a detection antibody or a solution comprising a detection antibody can be carried out by an individual or an automated device, such as an automated immunodiagnostic device. Methods for dispensing and contacting a solid phase with a detection antibody can include manually pipetting or placing a desired amount of detection antibody in the receptacle, and/or by way of robotic or automated dispensing mechanisms. In embodiments where the present methods are carried out, in-whole or in-part, by an automated immunodiagnostic, device, the detection antibody is first provided to a designated reservoir and an aliquot of the detection antibody is subsequently dispensed to a receptacle or multiple receptacles of a solid phase, which has been provided to the automated immunodiagnostic device.

In one embodiment, the methods of the present disclosure are carried out in one of the following automated immunodiagnostic devices Ortho Clinical Diagnostics VITROS® ECiQ, Ortho Clinical Diagnostics VITROS® 3600 or Ortho Clinical Diagnostics VITROS® 5600.

In some embodiments, the detection antibody dispensed into a receptacle and incubated for up to forty minutes. In a specific embodiment, the detection antibody dispensed into a receptacle and incubated for about 4, 5, 6, 7, 8, 9 or 10 minutes. In other embodiments, the detection antibody is incubated in a receptacle for 8 minutes.

In certain embodiments, the sample is premixed with the detection antibody prior to administering the sample and detection antibody mixture to a receptacle. In one embodiment, the sample and detection antibody mixture is incubated for 1-60 minutes, 1-50 minutes, 1-40 minutes, 1-30 minutes, 1-20 minutes or 1-10 minutes, inclusive. In another embodiment, the sample and detection antibody mixture is incubated for 1-8 minutes, inclusive.

A detectable signal is generated by the detection antibody present in each receptacle of a solid phase. The detectable signal can be generated, for example by a fluorometer that employs an excitation light source transducer, which is spatially separate from the solid phase, that directs the excitation light to each well being analyzed to produce a detectable wavelength of light in the well, which can be measured by an optical detector.

In yet other embodiments, antibody-based biosensors may also be employed to determine the presence or amount of analyte bound to detection antibodies present in a receptacle.

In a specific embodiment, each detection antibody is conjugated to the same detectable label, such as horseradish peroxidase and the detectable signal is produced, for example, by providing a substrate, such as a luminogenic substrate, to each well such that the HRP enzyme oxidizes the luminogenic substrate, which then emits a detectable signal (light).

In certain embodiments, the luminogenic substrate (e.g., luminol, a derivative thereof and a peracid salt) is provided with an electron-transfer agent (enhancer), such as a substituted acetanilide, to amplify the light signal emitted by the substrate, as well as prolong emission of the signal from the receptacle. In some embodiments, the luminogenic substrate is provided in a solution that includes an enhancer solution. In other embodiments, the luminogenic substrate is provided to a receptacle in a first solution and an enhancer is provided to the receptacle in a second solution.

In certain embodiments, the luminogenic substrate and electron-transfer agent are provided to a receptacle and incubated for about 1-20 minutes, 1-15 minutes, 1-10 minutes, 1-9 minutes, 1-8 minute, 1-7 minutes, 1-6 minutes, 1-5 minutes, 1-4, minutes, 1-3 minutes, 1-2 minutes or less than 1 minute. In a specific embodiment the luminogenic substrate and electron-transfer agent are provided to a receptacle and incubated for 4-5 minutes.

The methods provided herein further include detecting the presence of each of the analytes of interest. Generally, the detection step is carried out by measuring the amount of signal produced by each receptacle to which sample was provided.

The present methods can be deployed for the simultaneous or serial detection of two or more different analytes using a single solid phase with high sensitivity and minimal interference from the other analytes. Generally, the signal generated by the detection antibody, either directly or indirectly, after application of the sample to the solid phase can be detected visually or obtained by a device (analytical instrument), such as a reflectometer, a fluorometer, or a transmission photometer.

In some embodiments, when a signal is generated and detected (indicating the presence of an analyte in the sample), the signal is then measured and quantified. In specific embodiments the measured amount of signal in each receptacle is quantified to and provided as a single value. In other embodiments, the amount of signal measured in each receptacle correlates to the amount of an analyte present in the sample.

In some embodiments, the detected signal(s) can be compared to that generated after the use of a control sample in the present methods. Such a comparison can facilitate quantification of the amount of an analyte detected in a sample. In one instance, for quantitative measurements, calibration curves are fitted using a modified four- or five-parameter log-logistic software program, e.g., Ortho Clinical Diagnostics, Assay Data Disk (on VITROS® 3600 Immunodiagnostic System, VITROS® 5600 Integrated System) or a magnetic card (on VITROS® ECiQ device).

In certain embodiments, a single value can be provided that quantifies the total amount of all analytes of interest present in the sample. In one embodiment, the detected amount of a first analyte in a first receptacle is multiplied by the detected amount of a second analyte in a second receptacle and the total is then divided by 1000.

In certain aspects of the present disclosure, kits for performing the methods described herein are provided. Suitable kits comprise reagents sufficient for performing a method of the present disclosure, together with instructions for performing the described methods. Additional optional elements that may be provided as part of an assay kit are described herein.

In certain embodiments, reagents for performing the present methods are provided in a kit. Reagents of a kit include one or more of the following, a solid phase, antibodies, buffer solutions, a luminogenic substrate, an electron-transfer agent and instructions for performing the methods of the present disclosure.

A kit includes a solid phase having a plurality of receptacles coated with at least 2 capture antibodies. In specific embodiments, each receptacle of a solid phase provided in a kit has at least two different capture antibodies immobilized thereto, such that each of the at least two different capture antibodies recognize a different antigen or epitope (analyte).

In one embodiment, the solid phase provided in a kit includes a plurality of tapered receptacles, such as VITROS® Microwells. In another embodiment, a solid phase is provided that includes a straw or sleeve of at least 20 VITROS® Microwells. In another embodiment, a solid phase is provided that includes a straw or sleeve of at least 25 VITROS® Microwells. In a specific embodiment, the solid phase includes 25 VITROS® Microwells in a sealed straw.

In one embodiment, a kit of the present disclosure includes four solid phases each containing a straw or sleeve of at least 10 tapered receptacles. In another embodiment, a kit of the present disclosure includes four solid phases each containing a straw or sleeve of at least 20 tapered receptacles. In yet another embodiment, a kit of the present disclosure includes four solid phases each containing a straw or sleeve of 25 tapered receptacles. In one embodiment, a kit of the present disclosure includes four solid phases each containing a straw or sleeve of 25 VITROS® Microwells.

In some embodiments, a kit includes at least two different detection antibodies whereby each of the at least two different detection antibodies recognizes a different analyte of interest. In some embodiments, each of the at least two different detection antibodies include detectable labels that are the same or produce the same detectable signal.

In some embodiments, the detection antibodies are monoclonal antibodies, polyclonal antibodies, fragments thereof or any combination thereof. In specific embodiments, the detection antibodies are all monoclonal antibodies, which each recognize a different analyte of interest. In other embodiments, the detection antibodies are all polyclonal antibodies, which each recognize an analyte of interest. In yet another embodiment, the detection antibodies provided include a combination of monoclonal antibodies and polyclonal antibodies, each of which is specific to a different analyte of interest.

In some embodiments, a kit includes antibodies specific to TIMP2 and IGFP7, respectively. In certain embodiments, the detection antibodies of the present disclosure are monoclonal antibodies specific to TIMP2 and IGFBP7, respectively. In specific embodiments, the detection antibody that is specific to TIMP2 is monoclonal antibody 40H2-40K3, and the detection antibody that is specific to IGFBP7 is monoclonal antibody 6D2. 1.

In specific embodiments, a kit includes at least two different detection antibodies that each recognize a different analyte of interest and are conjugated to a detectable label. In one embodiment, the kit includes at least two different detection antibodies that each recognize a different analyte of interest and are each conjugated to horseradish peroxidase (HRP).

In some embodiments of the present disclosure, a kit includes a substrate, such as a luminogenic substrate. Luminogenic substrates for use in the present methods and kits are known by those of ordinary skill in the art, as are enhances thereof. As such, the specific combination(s) of enzyme, substrate and enhancer are not intended to be limiting. In certain embodiments, the luminogenic substrate provided in a kit is luminol or a derivative thereof and a peracid salt. In some embodiments, the kit includes an electron-transfer agent (enhancer), such as a substituted acetanilide, that is capable of amplifying a signal produced by the detectable label.

In some embodiments, kits of the present disclosure include a reference solution (calibration solution) that includes a known amount of a particular analyte of interest. In one embodiment, the reference solution can include a known amount or known amounts of at least 2 analytes of interest. In another embodiment, a reference solution can be provided for each corresponding analyte detected by such a kit.

In certain embodiments, the kits of the present disclosure include one or more solutions or buffers. For example, a kit can contain one or more of the following: phosphate buffer, detection antibody solution (e.g., TIMP2 detection antibody conjugate solution, IGFBP7 detection antibody conjugate solution), and water (e.g., deionized or sterile).

DETAILED DESCRIPTION

Figure 1:
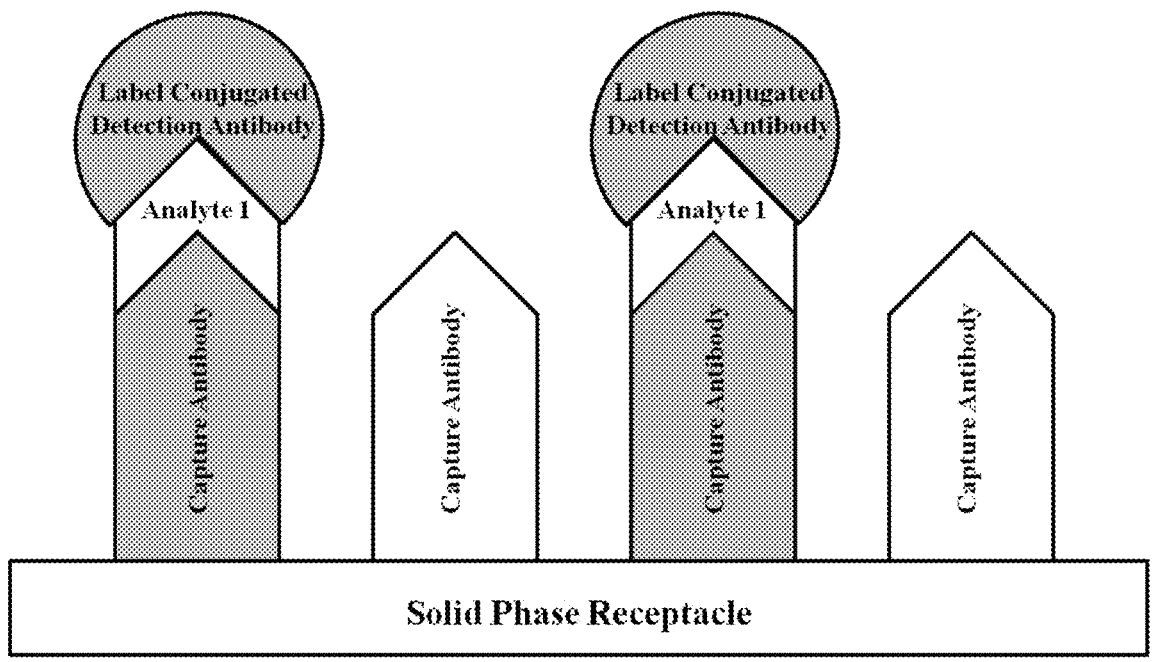
FIG. 1. A schematic of an exemplary solid phase receptacle of the present disclosure. The solid phase shown includes a receptacle having two different capture antibodies immobilized (bound) thereto. Each of the capture antibodies is specific to a distinct analyte, i.e., antigen (Analyte 1, Analyte 2), either of which may or may not be present in a sample. The schematic shows the ability of a capture antibody to bind a specific antibody present in a sample when a sample is provided to the receptacle, and further depicts the formation of a capture antibody-analyte-detection antibody complex after further introduction of a detection antibody of the present disclosure using the present methods.

The methods provided herein utilize a single solid phase that includes a plurality of receptacles each of which has at least two antibodies immobilized thereto. The antibodies, i.e., capture antibodies, recognize at least two different analytes of interest. Therefore, the methods provided herein facilitate the detection and measurement of multiple analytes using a single solid phase. The use of a single solid phase to detect multiple analytes eliminates costs associated with producing a separate solid phase for the quantitative detection of each specific analyte of interest. The methods of the present disclosure also improve efficiency by limiting the potential for user error by simplifying assays and reducing the amount of components necessary to detect multiple analytes in a sample. In addition, the present methods utilize labeled detection antibodies having the same detectable signal. This further simplifies the quantitative detection of multiple analytes by reducing the need for differentially detectable labels, and thus means for detecting multiple signals.

In a first aspect, the present disclosure provides methods for detecting the presence of analytes of interest in a sample. The methods include providing a solid phase that includes receptacles that are each coated with antibodies that bind (capture) the analytes of interest in a sample, if present, when contacted with a sample or a portion thereof. Each receptacle includes at least two different antibodies immobilized to a surface thereof, whereby at least two of the immobilized antibodies recognize a different analyte. A sample is provided to each receptacle, such that the sample or a portion thereof, comes in contact with the capture antibodies immobilized to each receptacle. When the sample contains an analyte (e.g., a protein of interest or fragment thereof, or a receptor of interest) recognized by an immobilized antibody, the analyte in the sample binds to the corresponding capture antibody present in the receptacle. The methods of the present disclosure also include providing an antibody that includes a detectable label (detection antibody) to each receptacle. The detection antibody provided to each receptacle is specific to one of the analytes of interest. However, each specific detection antibody provided produces the same detectable signal. The methods provided herein also include detecting the presence of each of the analytes of interest.

As used herein, the term "analyte" or "analytes" is any molecule that can be recognized by an antibody (e.g., an antigen, another antibody or portions thereof). In some embodiments, an analyte is a polypeptide. As used herein, a "polypeptide" is a single polymer chain of amino acids bonded together by peptide bonds between the carboxyl and amino groups of adjacent amino acid residues. The term "protein" includes polypeptide. The term "protein" may also be used to describe a polypeptide, having multiple domains, such as beta sheets, linkers and alpha-helices. As such, the term "protein" is also meant to include polypeptides having quaternary structures, ternary structures and other complex macromolecules composed of at least one polypeptide. If the protein is comprised of more than one polypeptide that physically associate with one another, then the term "protein" as used herein refers to the multiple polypeptides that are physically coupled and function together as the discrete unit. In embodiments where the analyte is another antibody, the analyte-antibody is any antibody that is different from a capture antibody that is capable of binding to a capture antibody.

In embodiments of the present methods, an analyte is any polypeptide that includes an epitope or amino acid sequence of interest. Such polypeptide can be present in a bodily fluid or solid samples. In some instances, the analyte is a polypeptide or antibody that is present on, within or produced by an organism (e.g., mammal, bacteria, viruses). In some embodiments, the analyte is a polypeptide or antibody that is present on, within or produced by or cells. In yet other embodiments, the analyte is a polypeptide or antibody that is synthetically produced, or recombinantly produced using means known by those of ordinary skill in the art.

For example, analytes can be prepared using the solid-phase synthetic technique initially described by Merrifield, J. Am. Chem. Soc. (1963) 85 pp. 2149-2154, for the production of polypeptides. Other polypeptide synthesis techniques can be found in M. Bodanszky, et al. Peptide Synthesis, John Wiley & Sons, 2d Ed., (1976) and other references readily available to those skilled in the art. A summary of polypeptide synthesis techniques can be found in J. Stuart and J. D. Young, Solid Phase Peptide Synthesis, Pierce Chemical Company, Rockford, Ill., (1984). Analytes may also be synthesized by solution methods as described in The Proteins, Vol. II. 3d Ed., Neurath, H. et al., Eds., pp. 105-237, Academic Press, New York, N.Y. (1976). Appropriate protective groups for use in different peptide syntheses are described in the above-mentioned texts as well as in J. F. W. McOmie, Protective Groups in Organic Chemistry, Plenum Press, New York, N.Y. (1973). The analytes of the present disclosure can also be prepared by chemical or enzymatic cleavage from larger portions of a protein or polypeptide.

In some embodiments, an analyte of the present methods is a protein or antibody or fragments thereof that have been produced by a cell. In certain embodiments, the analyte is a protein that is present on the outermost surface of the cellular membrane. In one embodiment, the protein present on the outermost surface of the cellular membrane has an antigen or epitope that is accessible to an antibody. In yet other embodiments, an analyte is a protein or a fragment thereof that has been secreted by a cell.

The format/approach disclosed herein by immobilizing multiple antibodies to capture and detect multiple antigens in a sample can be designed in a reverse format. As such, in certain embodiments, where the analytes to be detected in a sample are antibodies or fragments thereof, a solid phase can be provided that includes receptacles that are each coated with multiple antigens (e.g., peptides) that bind (capture) the antibodies (i.e., analytes) of interest in a sample, if present, when contacted with a sample or a portion thereof. For example, each receptacle includes at least two different antigens or peptides immobilized to a surface thereof, whereby at least two of the immobilized antigens each recognize a different antibody analyte. A sample is provided to each receptacle, such that the sample, or a portion thereof, comes in contact with the antigens immobilized to each receptacle. When the sample contains an analyte (e.g., an antibody of interest or fragment thereof) recognized by an immobilized antigen, the antibody in the sample binds to the corresponding capture agent (i.e., antigen) present in the receptacle. Such methods also include providing an antibody that includes a detectable label (detection antibody) to each receptacle. The detection antibody provided to each receptacle is specific to one of the analytes (antibodies) of interest or a portion thereof. However, each specific detection antibody provided produces the same detectable signal.

Additionally, the peptides (analytes) of the present disclosure can also be prepared by recombinant techniques known by those of ordinary skill in the art. See, e.g., Current Protocols in Molecular Cloning Ausubel et al., 1995, John Wiley & Sons, New York); Sambrook et al., 1989, Molecular Cloning: A Laboratory Manual, Second Edition, Cold Spring Harbor Laboratory Press, New York; and Coligan et al. (1994) Current Protocols in Immunology, John Wiley & Sons Inc., New York, N.Y. The skilled artisan understands that any of a wide variety of expression systems can be used to provide recombinant peptides. The precise host cell used is not critical to the instant methods. However, by way of example, the analytes of the present disclosure can be produced in a prokaryotic host (e.g., E. coli), in a eukaryotic host (e.g., S. cerevisiae) or mammalian cells, such as COS1, CHO, NIH3T3, and JEG3 cells, or in the cells of an arthropod, e.g., S. frugiperda.

In certain exemplary embodiments, an analyte is insulin-like growth factor-binding protein 7 (IGFBP7), a derivative, analog or homolog thereof. In certain embodiments, the IGFBP7 is any polypeptide that is derived from the Insulin-like growth factor-binding protein 7 precursor set forth, for example, in Accession Nos. NP_001240764.1, AAH66339, AAR89912 or AAP35300. In other embodiments, the analyte is any polypeptide fragment of an IGFBP7 protein that includes an epitope that can be recognized by an antibody.

In other exemplary embodiments, an analyte is an inhibitor of matrix metalloproteinase, a derivative, analog or homolog thereof. In certain embodiments, the analyte is a tissue-inhibitor of metalloproteinase (TIMP). In certain embodiments, the TIMP analyte is any polypeptide that is derived from the metalloproteinase inhibitor 2 (TIMP2) precursor set forth, for example, in Accession Nos. NP_003246.1, NP_035724.2, DAA18186.1 or NP_068824.1. In other embodiments, the analyte is any polypeptide fragment of a TIMP2 protein that includes an epitope that can be recognized by an antibody.

The term "homologs" means a corresponding polypeptide of another vertebrate species that is substantially homologous in amino acid sequence of, for example, human, rat, mouse, rabbit, bovine, canine or chicken. The term "analogs" is meant to encompass polypeptides that differ by one or more amino acids. Such as polypeptides that include an amino acid substitution(s), addition(s) or deletion(s), which do not abolish the ability of an antibody to recognize the polypeptide.

In some embodiments, the analytes of the present disclosure are at least 2, at least 3, at least 4, at least 5, at least 6 or more different proteins or polypeptides. In specific embodiments, the analytes of the present disclosure include at least two different polypeptides or proteins. In one embodiment, the analytes of the present disclosure include exactly two different polypeptides or proteins. In another embodiment, the methods of the present disclosure are employed to detect the presence or amount of TIMP2 and IGFBP7 (analytes) in a sample.

In other embodiments an analyte to be detected by the present methods is selected from the following, non-limiting list of polypeptides: prostate specific antigen (PSA), a molecule that forms a complex with PSA (e.g., $\alpha_2$-antichymotrypsin, at $\alpha_1$-protease inhibitor (API) or $\alpha_2$-macroglobulin), amyloid-β peptide (Aβ, βAP, AβP or β/A4), β-amyloid precursor protein (APP), tau microtubule protein, phospho-tau (e.g., tau protein phosphorylated at amino acid 181), isoforms, homologs, mutants forms or portions thereof. In some embodiments, the methods of the present disclosure are employed to detect the presence or amount of the following pairs of analytes: PSA and complexed-PSA; Aβ (or a mutant or portion thereof) and tau; and tau and phospho-tau.

Once the analytes of interest are determined an antibody specific to each of the analytes are selected for use in the methods of the present disclosure.

The term "antibody" as used herein, refers to an immunoglobulin molecule encoded by an immunoglobulin gene or genes, or a derivative thereof, which has the ability to bind to a specific antigen or epitope. See, e.g., Fundamental Immunology, 3rd Edition, W. E. Paul, ed., Raven Press, N.Y. (1993); Wilson et al., *J. Immunol. Methods* (1994) 175:267-273. By way of example, the variable regions of the heavy and light chains of the immunoglobulin molecule contain a binding domain that interacts with and binds an antigen (antigen-binding portion), as it has been shown that the antigen-binding function of an antibody may be performed by fragments of a full-length antibody, i.e., "antigen-binding fragments" or "antigen-binding portions". Examples of antigen-binding portions or antigen-binding fragments encompassed within the term "antibody" include, but are not limited to, (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (see, e.g., Ward et al., *Nature* (1989) 341 pp. 544-546), which consists of a VH domain; and (vi) an isolated complementarity determining region (CDR). As with full antibody molecules, antigen-binding portions may be monospecific or multispecific (e.g., bispecific). Single chain antibodies are also included by the term "antibody". The term antibody also includes monoclonal antibodies and polyclonal antibodies.

Therefore, in some embodiments, the antibodies of the present disclosure can be monoclonal, polyclonal, fragments thereof and any combination thereof. In specific embodiments, the antibodies of the present disclosure are all monoclonal antibodies, which each recognize an analyte of interest. In other embodiments, the antibodies of the present disclosure are all polyclonal antibodies, which each recognize an analyte of interest. In yet another embodiment, the antibodies of the present disclosure are a combination of monoclonal antibodies and a polyclonal antibody, each of which is specific to a different analyte of interest.

In some embodiments, the antibodies of the present disclosure include at least 2, at least 3, at least 4, at least 5, at least 6 or more different antibodies. In certain embodiments of the present methods, a solid phase includes 2, 3, 4, 5, 6, 7, 8, 9, 10, or more different antibodies that recognize different analytes. In some embodiments, the solid phase includes two or more different antibodies that are specific to only two different analytes. In specific embodiments, the solid phase includes two different antibodies each of which recognizes two different antigens or epitopes (analytes).

In another embodiment, the antibodies of the present disclosure are specific to TIMP2 and IGFP7, respectively. In some embodiments, the antibodies of the present disclosure are monoclonal antibodies specific to TIMP2 and IGFBP7, respectively. In other embodiments, the antibodies are mouse monoclonal antibodies, human monoclonal antibodies or rabbit monoclonal antibodies. In certain embodiments, the antibodies are mouse or rabbit monoclonal antibodies specific to TIMP2 and IGFBP7. In a specific embodiment, the antibody specific to TIMP2 is mouse monoclonal antibody 6E2.1, and the antibody specific to IGFBP7 is mouse monoclonal antibody 1D6.

In other embodiments, an antibody for use in the present methods is selected from the following, non-limiting list of antibodies: any monoclonal or polyclonal antibody that specifically recognizes tau (e.g., HT7 and AT270 monoclonal antibodies; antibodies recognizing normally and abnormally phosphorylated tau (e.g., Alz50 (Ghanbari et al., 1990), HT7 (Mercken et al., 1992) and AT120 (Vandermeeren et al., 1993)); any antibody recognizing PSA or a binding partner there of (e.g., 2E9, 2H11 and 5A10 as described in U.S. Pat. No. 5,501,983, the entire contents of which is incorporated herein by reference); any antibody that binds Aβ or a portion thereof, such as those described in U.S. Pat. No. 7,700,309, the entire contents of which are incorporated herein by reference; and other antibodies known to those of ordinary skill in the art such as, for example, those disclosed in U.S. Pat. No. 9,174,097, the entire contents of which is incorporated herein by reference.

Generally antibodies for use in the present methods, regardless of the analyte they recognize, fall into two categories: (i) capture antibodies, and (ii) detection antibodies. The term "capture antibody" or "capture antibodies" as used herein are antibodies that can be affixed (immobilized) to a portion or surface of a receptacle of a solid phase, which are capable of binding (capturing) an analyte of interest when contacted by a corresponding epitope present on or within the analyte. For example, capture antibodies are affixed to a receptacle of a solid phase such that the antigen-binding portion of the antibody is presented within the receptacle in a manner that permits binding to an antigen, if present.

The term "detection antibody" or "detection antibodies" as used herein means an antibody that is capable of binding to an analyte of interest when contacted by an epitope present on or within the analyte and is attached to (e.g., conjugated or linked) to a detectable label. A "detectable label" or "detection element" are used interchangeable herein to mean any molecule or molecules that are directly detectable (e.g., fluorescent moieties, electrochemical labels, electrochemical luminescence labels, metal chelates, colloidal metal particles), as well as a molecule or molecules that may be indirectly detected by production of a detectable reaction product (e.g., enzymes such as horseradish peroxidase, alkaline phosphatase and the like), a molecule or molecules that can be detected by recognition of a molecule that specifically binds to the detection antibody such as, a labeled antibody that binds to the detection antibody, biotin, digoxigenin, maltose, oligohistidine, 2,4-dintrobenzene, phenylarsenate, a nucleic acid (e.g., ssDNA, dsDNA) or the like). In a specific instance, the detectable label is horseradish peroxidase.

Capture antibodies for use in the present methods are provided on a surface of a receptacle of a solid phase. In certain embodiments, a first portion of a capture antibody of the present disclosure is affixed to a surface of a receptacle, such that an antigen-binding portion of the capture antibody is positioned such that the antigen-binding portion of the antibody can be contacted by an antigen presented thereto.

A capture antibody can be affixed to a receptacle present on or within a solid phase in a number of ways known to those of ordinary skill in the art. For example, a capture antibody can be covalently or non-covalently bound to a receptacle. In certain instances, the capture antibody can be either directly or indirectly attached to a surface of a receptacle. For example, a capture antibody can be directly covalently bound to a receptacle through a chemical bond between a portion of the capture antibody and a functional group on a surface of the solid phase receptacle. Alternatively, a capture antibody can be indirectly covalently bound to a solid phase receptacle by covalently binding the antibody to a linker and binding the linker to the solid phase receptacle. In some instances, a capture antibody is directly non-covalently bound to a solid phase receptacle through non-covalent association or adsorption of the antibody to the solid phase receptacle. In other instances, a capture antibody is indirectly non-covalently bound to a solid phase receptacle such that the antibody is covalently bound to a linker or other intermediate agent, which then forms a non-covalent bond with the solid phase receptacle. In all cases, association of a capture antibody with a receptacle should immobilize the capture antibody to the solid phase receptacle, or a portion thereof in a manner that exposes the antigen-binding portion of the antibody and does not affect or limit the specificity of the capture antibody, i.e., does not reduce the ability of the capture antibody to bind an analyte of interest when presented to the antibody.

A variety of chemical reactions useful for covalently attaching an antibody to a solid phase receptacle are well known to those skilled in the art. Illustrative examples of functional groups useful for covalent attachment of a capture antibody to a receptacle include alkyl, Si—OH, carboxy, carbonyl, hydroxyl, amide, amine, amino, ether, ester, epoxides, cyanate, isocyanate, thiocyanate, sulfhydryl, disulfide, oxide, diazo, iodine, sulfonic or similar groups having chemical or potential chemical reactivity. In a specific embodiment, the capture antibodies of the present disclosure are directly immobilized to a receptacle by adsorption.

An antibody can be non-covalently bound to a solid phase receptacle, such as through adsorption to or coating on the receptacle, or through covalent or non-covalent association with a linker or binding agent which itself is non-covalently bound or immobilized to the receptacle. Illustrative examples of linkers or binding agents useful for association of antibodies to a solid phase include proteins, organic polymers (e.g., PEG and derivatives thereof), and small molecules. More specific examples of linkers useful for immobilizing antibodies of the present disclosure to a solid phase include Human Serum Albumin (HAS), Bovine Serum Albumin (BSA), streptavidin, avidin, biotin, PEG, and antibodies or antibody fragments.

In one non-limiting example, a capture antibody can be covalently conjugated to a binding agent such as HSA or BSA, and then the resulting conjugate can be used to coat a receptacle. In another embodiment, an antibody can be covalently conjugated to one of streptavidin, biotin or avidin: the conjugated antibody can then bind to a different streptavidin, biotin or avidin molecule, which is immobilized to a receptacle.

In some embodiments, a surface of the solid phase receptacle can be modified to facilitate the stable attachment (immobilization) of capture antibodies to the receptacle. Generally, a skilled artisan can use routine methods to modify a receptacle in a manner that facilitates the immobilization of an antibody to a surface thereof. The following are non-limiting examples of applicable modifications.

The surface of the solid phase receptacles can be coated to facilitate attachment of an antibody. In general, the coating will be one that is complementary to a portion of the antibody. The surface of a receptacle can be amidated by silylating the surface, such as with trialkoxyaminosilane. Silane-treated receptacles can also be derivatized with homobifunctional and heterobifunctional linkers. A receptacle surface can be derivatized such that the receptacle includes a hydroxy, an amino (e.g., alkylamine), carboxyl group, N-hydroxy-succinimidyl ester, photoactivatable group, sulfhydryl, ketone, or other functional group available for reaction. Illustrative examples of a molecule useful for non-covalent attachment of antibodies to a receptacle of a solid phase include agents that are capable of binding to antibodies such as, but not limited to, staphylococcal protein A or protein G.

In other embodiments, a solid phase receptacle includes functional groups that are incorporated into the material of a receptacle. Illustrative examples of functional groups useful for covalent attachment of an antibody to a receptacle include alkyl, Si—OH, carboxy, carbonyl, hydroxyl, amide, amine, amino, ether, ester, epoxides, cyanate, isocyanate, thiocyanate, sulfhydryl, disulfide, oxide, diazo, iodine, sulfonic or similar groups having chemical or potential chemical reactivity.

In an exemplary embodiment, such as that shown in FIG. 1, capture antibodies are immobilized to a surface of a solid phase receptacle by adsorption. More specifically, a solid phase having a plurality of receptacles are each coated with polystyrene and irradiated.

The proper amount of irradiation can be determined by one of ordinary skill such that the amount of radiation provided to the solid phase maximizes adsorption of a capture antibody. In certain embodiments, the receptacles of a solid phase can be irradiated to 1.0 MRad to 3.5 MRad, inclusive. In other embodiments, the receptacles are irradiated to about 1.0 MRad, about 1.5 MRad, about 2.0 MRad, about 2.5 MRad, about 3.0 MRad, or about 3.5 MRad. In a specific embodiment, the receptacles have been irradiated to about 1 MRad. Receptacles irradiated to about 1MRAD display an improved ability to immobilize monoclonal capture antibodies to an irradiated surface.

A capture antibody-coating solution that includes, for example, phosphate, sodium chloride and buffer at a pH that has been optimized to prohibit denaturing of the antibodies (e.g., pH of about 5.5 to 9.0, or more specifically a pH of about 6.0-7.0), as well as at least two different capture antibodies are dispensed in each receptacle of a solid phase such that an innermost surface of each receptacle is contacted with antibody-coating solution. The solid phase receptacles are then incubated to facilitate adsorption of the capture antibodies in solution. The solid phase receptacles are then washed in order remove an unattached antibody from the receptacles. Washing can occur one, two, three, four or more times. However, minimizing the amount of washes will reduce the time and cost of producing a solid phase. In some instances, washing a solid phase twice is sufficient to remove all excess antibodies from the receptacles. A post-coat solution that includes, for example, Tris/HCL, sucrose, NaCl and serum albumin are dispensed in each receptacle such that the antibody-coated surface of each receptacle is contacted with post-coat solution. After incubation with post-coat solution, the post-coat solution is removed, such as by aspiration, the receptacles are dried and stored for future use. As shown in FIG. 1, the foregoing results in the immobilization of multiple capture antibodies to a surface of a solid phase receptacle, such that the antibodies are orientated with their antigen-binding regions exposed.

As used herein, the term "solid phase" refers to any solid or semi-solid material with which two or more receptacles can be incorporated. By way of example, a solid phase provides material to which receptacles can be attached and dispensed from. Suitable solid phase materials are known in the art. A solid phase can be composed of a single material or a variety materials including, but not limited to, a natural or synthetic polymer, resin, metal, silicate or combinations thereof, so long as the material or combination of materials in the solid phase does not prohibit attachment or incorporation of receptacles or interfere with any step of the methods provided herein.

A non-exhaustive list of suitable materials for a solid phase include agaroses; celluloses such as carboxymethyl cellulose; dextrans, such as Sephadex®; polyacrylamides: polystyrenes; polyethylene glycols; resins; silicates; divinylbenzenes; methacrylates; polymethacrylates; glass; ceramics; papers; metals; metalloids: polyacryloylmorpholidse; polyamides; poly(tetrafluoroethylenes); polyethylenes; polypropylenes; poly(4-methylbutenes); poly(ethylene terephthalates); rayons; nylons; poly(vinyl butyrates); poly-vinylidene difluorides (PVDF); silicones; polyformaldehydes; cellulose acetates; nitrocellulosse, or combinations of two or more of any of the foregoing.

In some embodiments, the solid phase used in the present methods is composed of polystyrene.

A solid phase can have a variety of formats, which can include, for example, a membrane; a chip; a plate, a straw; a sleeve; a slide; a column; a hollow, solid, semi-solid, pore or cavity containing particle such as a bead; a gel; a fiber including a fiber optic material; and a matrix. In certain embodiments, the solid phase comprises a chip; a plate, a straw; a sleeve; a slide; a column; or a matrix that includes a plurality of receptacles. In certain embodiments, the solid phase comprises a straw or a sleeve that includes at least 2 receptacles.

The term "receptacle" or "receptacles" are used to define a subset of a solid phase that is capable of receiving and containing a volume of solution, sample or other material. Non-limiting examples of receptacles include cups, wells, tubes, capillaries, vials and any other vessel, groove or indentation capable of holding a solution, a sample or a portion thereof. A receptacle can be contained in a solid phase, such as part of a straw, sleeve, a strip, a plate, a slide, a column, a matrix or the like. Specifically, a plurality of receptacles can be included in or on a solid phase, such as a straw or strip including cups or wells, a multiwell plate, a microwell plate or the like, which can be used in an automated immunodiagnostic devices.

In one embodiment, a solid phase for use in the present methods includes receptacles with vertical sidewalls that are tapered from top to bottom, such that the bottom portion of the receptacle has a width that is less than the width of an upper portion of the receptacle. For example, the tapered receptacles are conical or cup shaped. Tapered receptacles such as those shown in FIG. 2, improve the efficiency of the present methods by, for example, reducing the duration of incubation periods and the amount of material (e.g., solution, antibody, sample) used throughout the present methods. In a specific embodiment, the solid phase utilized in the present methods includes a plurality of VITROS® Microwells.

In some embodiments of the present methods, a solid phase includes a plurality of receptacles. In certain embodiments, the solid phase includes at least 2 receptacles, at least 3 receptacles, at least 4 receptacles, at least 5 receptacles, at least 6 receptacles, at least 7 receptacles, at least 8 receptacles, at least 9 receptacles, at least 10 receptacles, at least 15 receptacles, at least 20 receptacles, at least 25 receptacles or more. In an embodiment, a solid phase used in the present methods includes at least 2 receptacles. In other embodiments, the solid phase includes at least 2 tapered receptacles. In yet another embodiment, the solid phase includes a straw or sleeve of at least two VITROS® Microwells.

In certain embodiments of the present methods, a solid phase includes from 2 to 100 receptacles, 2 to 90 receptacles, 2 to 80 receptacles, 2 to 70 receptacles, 2 to 50 receptacles, 2 to 60 receptacles, 2 to 50 receptacles, 2 to 40 receptacles, 2 to 30 receptacles, 2 to 20 receptacles or 2 to 10 receptacles, inclusive. In some embodiments, the solid phase includes 2-100, 2-75, 2-50, 2-25, 2-15, 2-10 or 2-5 receptacles. In other embodiments, the solid phase includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 receptacles. In one embodiment the solid phase includes 25 tapered receptacles. In specific embodiments, the solid phase includes 25 receptacles in a straw or sleeve. In a specific embodiment, the solid phase includes 25 VITROS® Microwells in a sealed straw.

As described herein, two or more capture antibodies are associated with a surface of each receptacle of a solid phase support depending on the number of analytes detected by the present methods. In certain embodiments, each receptacle of a solid phase has at least 2, at least 3, at least 4, at least 5, at least 6 or more different capture antibodies immobilized thereto. In certain embodiments of the present methods, each receptacle of a solid phase has 2, 3, 4, 5, 6, 7, 8, 9, 10, or more different capture antibodies immobilized thereto. In specific embodiments, each receptacle of a solid phase has at least two different capture antibodies immobilized thereto, such that each of the at least two different capture antibodies recognize a different antigen or epitope (analyte). In embodiments, such as that exemplified in FIGS. 1 and 2, each receptacle of a solid phase has exactly two different types of capture antibodies immobilized to a surface thereof, such that each type of capture antibody recognizes a different analyte.

In other embodiments, a capture antibody for use in the present methods is selected from the following, non-limiting list of antibodies: any monoclonal or polyclonal antibody that specifically recognizes tau (e.g., HT7 and AT270 monoclonal antibodies; antibodies recognizing normally and abnormally phosphorylated tau (e.g., Alz50 (Ghanbari et al., 1990), HT7 (Mercken et al., 1992) and AT120 (Vandermeeren et al., 1993)); any antibody recognizing PSA or a binding partner there of (e.g., 2E9, 2H11 and 5A10 as described in U.S. Pat. No. 5,501,983, the entire contents of which is incorporated herein by reference); any antibody that binds Aβ or a portion thereof, such as those described in U.S. Pat. No. 7,700,309, the entire contents of which is incorporated herein by reference; and other antibodies known to those of ordinary skill in the art such as, for example, those disclosed in U.S. Pat. No. 9,174,097, the entire contents of which is incorporated herein by reference.

In some embodiments, at least one of the capture antibodies immobilized to the solid phase is a monoclonal antibody, a polyclonal antibody or a fragment thereof. In some embodiments, the capture antibodies immobilized to the solid phase are polyclonal antibodies or a fragment thereof. In other embodiments, capture antibodies are monoclonal antibodies.

In the exemplary embodiment shown in FIG. 1, each receptacle has a plurality of capture antibodies that recognize a first analyte and a plurality of capture antibodies that recognize a second antibody. In a specific embodiment, such as that shown in FIG. 3, each receptacle has at least 1 capture antibody that recognize a TIMP2 analyte, and at least 1 capture antibodies that binds an IGFBP7 analyte immobilized to a surface thereof. In certain specific embodiments, the TIMP2 and IGFBP7 capture antibodies are monoclonal antibodies or a fragment thereof. In certain embodiments, the capture antibodies immobilized to each receptacle of a solid phase are mouse monoclonal antibodies specific to TIMP2 and IGFBP7. In a specific embodiment, the capture antibody specific to TIMP2 is mouse monoclonal antibody 6E2.1 and the capture antibody specific to IGFBP7 is mouse monoclonal antibody 1D6.

In certain embodiments of the present methods, a sample or a portion thereof is provided to a solid phase including a plurality of receptacles therein, whereby each receptacle of the solid phase includes at least 2 capture antibodies that are each capable of binding a different analyte.

Regardless of the number of analytes or method for obtaining the analytes of interest, the analytes are provided to a sample or included within a sample, which can be readily applied to a solid phase. In certain embodiments, a sample may be obtained from a subject, or may be obtained from other materials. The term "subject" as used herein refers to a human or non-human organism. Thus, the methods described herein are applicable in both human and veterinary fields. Further, while a subject is preferably a living organism, the methods described herein may be used in post-mortem analysis as well. Subjects that are humans can be "patients," which as used herein refers to living humans that are receiving or may receive medical care for a disease or condition.

In some instances, the sample is created for the purpose of determining the presence of certain analytes therein. For example, a sample may be obtained from cell culture, a fluid or tissue known to include, or not include, the analyte(s) of interest. In other instances, the sample is created by adding synthetic or recombinantly produced peptides to a solution that is easily stored and dispensed.

In specific embodiments, samples for use in the present methods are body fluid samples obtained from a subject, such as a patient. In some embodiments, samples of the present disclosure include blood, tears serum, plasma, cerebrospinal fluid, urine, saliva, sputum, and pleural effusions. One of skill in the art would realize that certain samples would be more readily analyzed following processing, e.g., fractionation or purification. For example, fractionation of whole blood obtained from a subject into serum and/or plasma components. Hence, a sample can be used as is, or can be treated to result in a final sample for detection of analytes. For example, a sample can be liquefied, concentrated, dried, diluted, lyophilized, extracted, fractionated, subjected to chromatography, purified, acidified, reduced, degraded, subjected to enzymatic treatment, or otherwise treated in ways known to those having ordinary skill in the art in order to release an analyte of interest. If desired, a sample can be a combination (pool) of samples, e.g., from an individual or from a manufacturing process.

A sample can be in a variety of physical states, such as liquid, solid, emulsion, or gel. Samples can be treated with customary care to preserve analyte integrity. Treatment can include the use of appropriate buffers and/or inhibitors, such as inhibitors of certain biological enzymes. One having ordinary skill in the art will be able to determine the appropriate conditions given the analytes of interest and the nature of the sample.

In a specific embodiment, the sample analyzed is a urine sample obtained from a subject. In one embodiment, the sample analyzed is a human urine sample obtained from a subject.

In some instances, the present methods will use multiple portions of a single sample. For example, a sample (e.g., blood, urine or other bodily fluid) is obtained from a subject as an initial volume. The initial sample volume can then be separated into 1 or more aliquots, such that each individual aliquot can be treated, processed, stored and/or analyzed using the methods disclosed herein.

Figure 2:
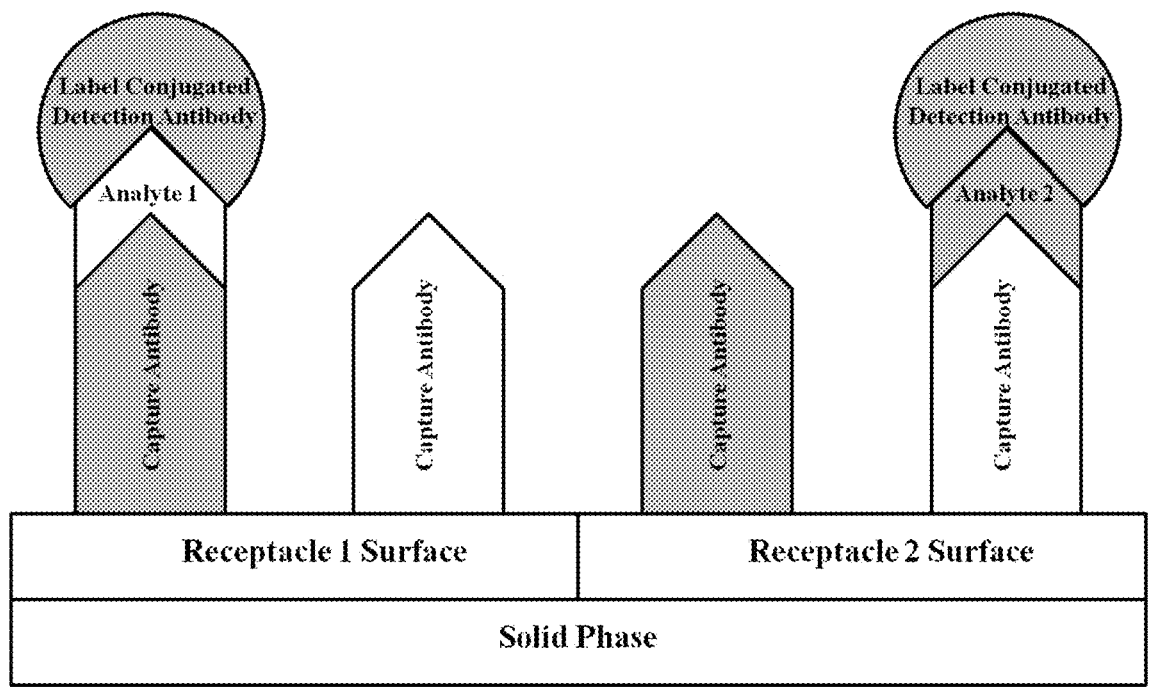
FIG. 2. A schematic depiction of an exemplary embodiment of the present methods for detecting multiple analytes in a sample. The schematic shows a method for detecting a first and second analyte in a sample that includes providing a solid phase holding at least two receptacles, each of which has two different capture antibodies immobilized to a surface of each receptacle. The depicted method shows that when sample is provided to each receptacle a specific detection antibody conjugated to a detectable label is also provided. While the label conjugated to each detection antibody shown is the same, the detection antibody provided to receptacle 1 recognizes only the first analyte, but the detection antibody provided to receptacle 2 recognizes the second analyte that is different from the first analyte. The amount of each analyte present in the sample is detected by measuring the detectable signal produced by the detection antibody present in each well. This enables quantification of the measured amount of each of the two analytes of interest in a sample. Here, the amount of the first analyte present in the sample is directly proportional to the amount of signal detected in receptacle 1, and the amount of the second analyte present in the sample is directly proportional to the amount of signal detected in the second receptacle.

Regardless of the type of sample used in the present methods, an amount of the sample is provided to each receptacle of a solid phase such that the sample comes in contact with the capture antibodies immobilized to a surface of each receptacle. As shown in FIG. 2, receptacles 1 and 2 of the solid phase include a first capture antibody and a second capture antibody affixed (immobilized) to each receptacle. The method exemplified in FIG. 2 also shows that each capture antibody recognizes and binds a different analyte of interest when compared to the other capture antibody (e.g., analyte 1 and analyte 2). Next, FIG. 2 shows that when a portion of a sample is administered to each receptacle, such that the sample containing (or not) an analyte of interest comes into contact with the corresponding capture antibody present on a surface of each receptacle, the antigen (analyte) present in the sample binds that particular capture antibody.

One of ordinary skill in the art can readily determine the appropriate amount of sample to provide to each receptacle.

In specific embodiments, the amount of sample dispensed into each receptacle can be different or the same. Determination of the amount of sample to deposit in each receptacle will depend on various factors, such as the type of sample, the type of analyte of interest, the type and shape of receptacle, the detection method employed and/or the type of antibodies used.

For example, the amount of a liquid sample provided to a receptacle can be from 1-10 mL, 1-5 mL, 1-4 mL, 1-3 mL, 1-2 mL or less than 2 mL of sample. In some embodiments, the amount of liquid sample is from 1-100 µL, 1-50 µL, 1-40 µL, 1-30 µL, 1-20 µL, 1-10 µL, 1-5 µL or less of sample. In certain embodiments, amount of sample provided to each receptacle is from 5 µL to 100 µL, 10 µL to 100 µL, 20 µL to 100 µL, 30 µL to 100 µL, or 40 µL to 100 µL. In other embodiments, the amount of sample provided to each receptacle is from 10 µL to 80 µL, 20 µL to 80 µL, 25 µL to 80 µL, 30 µL to 80 µL, 35 µL to 80 µL, or 40 µL to 80 µL. In a specific embodiment the amount of sample provided to a receptacle is from 10 µL to 80 µL, inclusive.

In yet other embodiments, the amount of liquid sample provided to each receptacle is about 10 µL, 20 µL, 25 µL, 30 µL, 35 µL 40 µL, 45 µL, 50 µL, 55 µL, 60 µL, 65 µL, 70 µL, 75 µL, 80 µL or more. In some embodiments, the amount of sample provided to each receptacle is exactly 20 µL, 25 µL, 30 µL, 35 µL, 40 µL, 45 µL, 50 µL, 55 µL, 60 µL, 65 µL, 70 µL, 75 µL or 80 µL. In a specific embodiment, the amount of liquid sample provided to each receptacle is 20 µL or 35 µL. In one embodiment, the amount of sample provided to each receptacle is 80 µL.

In some embodiments, the amount of liquid sample provided to each receptacle is about 1 µL, 2 µL, 3 µL, 4 µL, 5 µL, 6 µL, 7 µL, 8 µL, 9 µL, 10 µL, 11 µL, 12 µL, 13 µL, 14 µL, 15 µL, 16 µL, 17 µL, 18 µL, 19 µL, 20 µL, 21 µL, 22 µL, 23 µL, 24 µL, 25 µL, 26 µL, 27 µL, 28 µL, 29 µL, 30 µL, 31 µL, 32 µL, 33 µL, 34 µL, 35 µL, 36 µL, 37 µL, 38 µL, 39 µL, 40 µL, 41 µL, 42 µL, 43 µL, 44 µL, 45 µL, 46 µL, 47 µL, 48 µL, 49 µL, 50 µL, 51 µL, 52 µL, 53 µL, 54 µL, 55 µL, 56 µL, 57 µL, 58 µL, 59 µL, 60 µL, 61 µL, 62 µL, 63 µL, 64 µL, 65 µL, 66 µL, 67 µL, 68 µL, 69 µL, 70 µL, 71 µL, 72 µL, 73 µL, 74 µL, 75 µL, 76 µL, 77 µL, 78 µL, 79 µL, 80 µL, or more.

In certain embodiments, the sample is urine (e.g., human urine) and the amount of urine provided to each receptacle is from 5 µL to 100 µL, 10 µL to 100 µL, 20 µL to 100 µL, 30 µL to 100 µL, or 40 µL to 100 µL. In other embodiments, the amount of urine provided to each receptacle is from 20 µL to 80 µL, 25 µL to 80 µL, 30 µL to 80 µL, 35 µL to 80 µL, or 40 µL to 80 µL. In yet other embodiments, the amount of urine sample provided to each receptacle is about 20 µL, 25 µL, 30 µL, 35 µL, 40 µL, 45 µL, 50 µL, 55 µL, 60 µL, 65 µL, 70 µL, 75 µL, 80 µL or more. In some embodiments, the amount of urine sample provided to each receptacle is exactly 20 µL, 25 µL, 30 µL, 35 µL, 40 µL, 45 µL, 50 µL, 55 µL, 60 µL, 65 µL, 70 µL, 75 µL or 80 µL. In a specific embodiment, the amount of urine sample provided to each receptacle is 20 µL or 35 µL. In one embodiment, the amount of urine sample provided to each receptacle is 80 µL.

A sample or a portion thereof can be administered to a receptacle by any means known to one of ordinary skill in the art. Non-limiting examples of ways to administer a sample include dispensing by, for example, injecting, spraying or pouring the sample or a portion thereof to a receptacle. Means for dispensing and contacting a solid phase with a sample can include manually pipetting, washing, robotic or automated dispensing mechanisms, or other methods known to those having ordinary skill in the art. Routine care in the methods of administering a sample such as, the use of sterile techniques or other methods to preserve sample integrity are understood by those of ordinary skill in the art.

Administration of a sample or a portion thereof can be carried out by an individual or an automated device, such as an automated immunodiagnostic device. In embodiments where the present methods are carried out, in-whole or in-part, by an automated immunodiagnostic, device, the sample is first provided to a designated reservoir and a portion of the sample is subsequently dispensed to a receptacle or multiple receptacles of a solid phase, which has been provided to the automated immunodiagnostic device. Suitable automated immunodiagnostic devices for use in the present methods are known in the art. For example, certain automated immunodiagnostic devices are described in U.S. Pat. Nos. 7,312,084, 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety.

In specific embodiments, the automated immunodiagnostic device is: Ortho Clinical Diagnostics VITROS® ECiQ, Ortho Clinical Diagnostics VITROS® 3600, Ortho Clinical Diagnostics VITROS® 5600, Beckman ACCESS®, Abbott AXSYM®, Roche ELECSYS®, or Dade Behring STRATUS® devices.

In one embodiment, the methods of the present disclosure are carried out in one of the following automated immunodiagnostic devices: Ortho Clinical Diagnostics VITRO® ECiQ, Ortho Clinical Diagnostics VITROS® 3600 or Ortho Clinical Diagnostics VITROS® 5600.

A sample may be provided to a receptacle of a solid phase alone or in a mixture that includes a detection antibody.

Regardless of the type, form, amount or way in which a sample is provided to a receptacle the sample or a portion thereof is incubated in the receptacle in order to enable binding of the capture antibodies immobilized to a surface of the receptacle to any corresponding analytes that may be present in the sample. Specifically, once sample containing analytes of interest, is provided to each receptacle, as shown in FIG. 2, each receptacle will contain a first capture antibody bound to a first analyte of interest (analyte 1) and a second capture antibody that is bound to a different analyte of interest (analyte 2), creating a plurality of capture antibody-analyte complexes that are affixed to each receptacle. In instances, where only one type of analyte of interest is present in the sample provided, the capture antibody for that particular analyte will not be bound to the sample.

In some embodiments, the sample is provided to a receptacle and incubated for a period of time to facilitate the binding of any analytes of interest present in the sample to a corresponding capture antibody present on each receptacle. The incubation period can be readily determined by one of ordinary skill in the art and can vary based on the various factors, such as the type of sample, the type of analyte of interest, the type and shape of receptacle, the detection method employed and/or the type of antibodies used.

In certain embodiments, the sample is incubated in a receptacle in the absence of a detection antibody for about 1-60 minutes, 1-50 minutes, 1-40 minutes, 1-30 minutes, 1-20 minutes, 1-15 minutes, 1-10 minutes, 1-5 minutes, 1-4, minutes, 1-3 minutes, 1-2 minutes or less than 1 minute. In one embodiment, the sample dispensed into a receptacle in the absence of a detection antibody and incubated for 1-5 minutes, inclusive. In other embodiments, the sample is incubated in a receptacle for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes. In another embodiment, the sample dispensed into a receptacle in the absence of a detection antibody and incubated for 1, 2, 3, 4 or 5 minutes.

In certain embodiments, the sample is dispensed into a receptacle along with a detection antibody and the mixture is incubated for about 1-60 minutes, 1-50 minutes, 1-40 minutes, 1-30 minutes, 1-20 minutes, 1-15 minutes, 1-10 minutes, 1-8 minutes, 1-5 minutes, 1-4, minutes, 1-3 minutes, 1-2 minutes or less than 1 minute. In one embodiment, the sample and detection antibody mixture dispensed into a receptacle is incubated for 1-10 minutes, inclusive. In another embodiment, the sample and detection antibody mixture dispensed into a receptacle is incubated for 1-8 minutes, inclusive. In other embodiments, the sample mixed with the detection antibody in a receptacle and is incubated for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes. In yet other embodiments, the sample and detection antibody mixture dispensed into a receptacle is incubated for 1, 2, 3, 4, 5, 6, 7, 8, 9 or 10 minutes. In a specific embodiment, the sample and detection antibody mixture dispensed into a receptacle is incubated for 8 minutes.

The methods of the present disclosure also include separately providing detection antibodies to each receptacle of a solid phase. More specifically, the present methods include providing an amount of a detection antibody that recognizes a first analyte of interest to a first receptacle of a solid phase and providing an amount of another detection antibody that recognizes a different analyte of interest to another receptacle of the solid phase. In any event, the detection antibodies provided to each receptacle of a solid phase correspond to only one of the analytes of interest present (or not) in a sample and each include a detectable label that produces the same detectable signal.

As shown in FIG. 2, receptacles 1 and 2 of the solid phase include a first capture antibody and a second capture antibody affixed (immobilized) to each receptacle. Each capture antibody recognizes and binds a different analyte of interest when compared to the other capture antibody (e.g., analyte 1 and analyte 2). When sample is administered to each receptacle, such that the sample comes into contact a capture antibody present on a surface of each receptacle, the antigen (analyte) if present in the sample binds to the corresponding capture antibody specific to the analyte. This creates a plurality of capture antibody-analyte complexes immobilized to each receptacle. In instances where only one type of analyte of interest is present in the sample provided, the capture antibody for the analyte that is not present but being assayed for, will not be bound to the sample. Each receptacle is then provided an amount of a detection antibody specific to only one of the analytes of interest, i.e., either analyte 1 or analyte 2. This creates a plurality of capture antibody-analyte-detection antibody complexes immobilized to each receptacle, whereby only one specific analyte is detectably labeled in each well (e.g., analyte 1 or analyte 2). For example, as shown in FIG. 2, receptacle 1 includes only capture antibody-analyte 1-detection antibody complexes and the second receptacle includes only capture antibody-analyte 2-detection antibody complexes.

In some embodiments of the present methods, the detection antibodies are monoclonal antibodies, polyclonal antibodies, fragments thereof or any combination thereof. In specific embodiments, the detection antibodies of the present disclosure are all monoclonal antibodies, which each recognize an analyte of interest. In other embodiments, the detection antibodies of the present disclosure are all polyclonal antibodies, which each recognize an analyte of interest. In yet another embodiment, the detection antibodies of the present disclosure are a combination of monoclonal antibodies and polyclonal antibodies, each of which is specific to a different analyte of interest.

In some embodiments of the present methods, the detection antibodies are specific to TIMP2 and IGFP7, respectively. In certain embodiments, the detection antibodies of the present disclosure are monoclonal antibodies specific to TIMP2 and IGFBP7, respectively. In certain embodiments, a detection antibody provided to a receptacle of a solid phase is a monoclonal antibody that is specific to TIMP2, such as rabbit monoclonal 40H2-40K3 and the detection antibody provided to another receptacle of the solid phase is a mouse monoclonal antibody that is specific to IGFBP7, such as 6D2. 1.

In other embodiments, a detection antibody for use in the present methods is selected from the following, non-limiting list of detection antibodies: any monoclonal or polyclonal antibody that specifically recognizes tau (e.g., HT7 and AT270 monoclonal antibodies; antibodies recognizing normally and abnormally phosphorylated tau (e.g., Alz50 (Ghanbari et al., 1990), HT7 (Mercken et al., 1992) and AT120 (Vandermeeren et al., 1993)); any antibody recognizing PSA or a binding partner there of (e.g., 2E9, 2H11 and 5A10 as described in U.S. Pat. No. 5,501,983, the entire contents of which is incorporated herein by reference); any antibody that binds Aβ or a portion thereof, such as those described in U.S. Pat. No. 7,700,309, the entire contents of which is incorporated herein by reference; and other antibodies known to those of ordinary skill in the art such as, for example, those disclosed in U.S. Pat. No. 9,174,097, the entire contents of which is incorporated herein by reference.

As described herein, the detection antibodies used in the present methods include the same detectable label or detectable labels that produce the same detectable signal. This aspect of the present methods simplifies the detection of multiple analytes by reducing the need for a user to obtain detection antibodies with differentially detectable labels, as well as means for detecting multiple different signals.

Detectable labels are known to those of ordinary skill in the art as are means for conjugating such labels to an antibody. In some embodiments, the detectable label associated with a detection antibody is directly detectable. In certain embodiments, the directly detectable label is a fluorescent moiety (dye), an electrochemical label, an electrochemical luminescence label, metal chelates, or a colloidal metal particle. In other embodiments, the detectable label is an indirectly detectable label, such as a molecule that is detectable after it is subjected to a chemical or enzymatic reaction, or bound by a molecule that itself provides a detectable signal. In some embodiments, the detectable label is an enzyme, such as horseradish peroxidase or alkaline phosphatase, which can contact a substrate (e.g., chemiluminescent substrates (luminogenic substrate, such as 5-Amino-2,3-dihydrophthalazine-1,4-dione (luminol)), chromogenic substrates (e.g., 3,3',5,5'-Tetramethylbenzidine (TMB), 3,3'-Diaminobenzidine (DAB), 2,2'-azino-bis(3-ethylbenzothiazoline-6-sulphonic acid) (ABTS)) and oxidize the substrate to provide a detectable signal.

Figure 3:
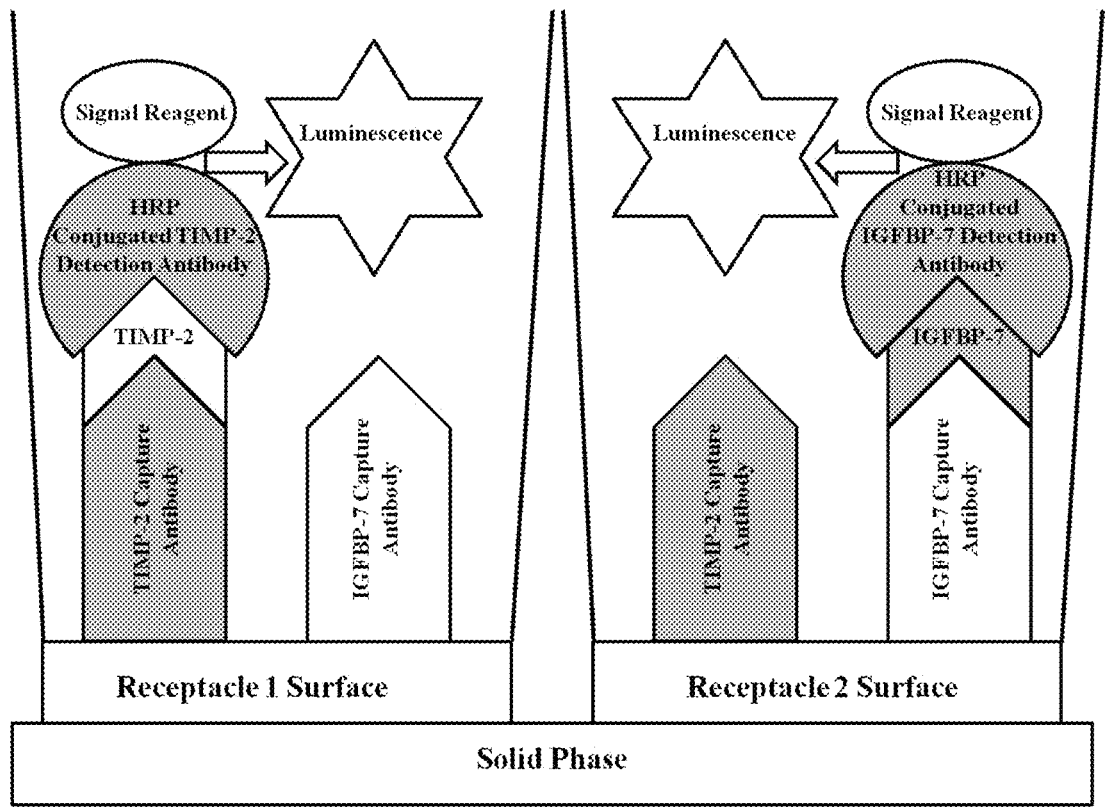
FIG. 3. A schematic depiction of a second exemplary embodiment of the present methods for detecting multiple analytes in a sample. The depicted method shows the detection of two analytes (TIMP2, IGFBP7) using a solid phase having tapered receptacles (receptacle 1, receptacle 2), each of which has capture antibodies specific to TIMP2 and capture antibodies specific to IGFBP7 immobilized to the inner surface of thereof. Sample is dispensed into receptacle 1 and a TIMP2-horseradish peroxidase (HRP)-conjugated detection antibody is dispensed into receptacle 1. Sample is dispensed into receptacle 2 and an IGFBP7-HRP-conjugated detection antibody is dispensed into receptacle 2. The contents of receptacle 1 and receptacle 2 are incubated at 37° C. and each receptacle is washed. The schematic also depicts an embodiment of the present methods whereby a signal reagent is provided to each receptacle after the formation of capture antibody-analyte-detection antibody complexes in each receptacle, which facilitates the emission of a detectable signal in the well. Here, a signal reagent including a luminogenic substrate and a signal enhancer is added to each receptacle and light emission (luminescence) is detected from each receptacle using a luminometer to measure the amount of light emitted from each receptacle. The amount of light signal detected in each receptacle is directly proportional to the concentration of TIMP2 and IGFBP7 present in the sample.

In some embodiments, a detectable label is attached to a detection antibody. In specific embodiments, the detectable label is conjugated to the detection antibody. In certain embodiments, the detectable label is a dye or enzyme that is conjugated to each detection antibody. In one embodiment of the present methods, horseradish peroxidase (HRP) is used as a conjugate with each specific detection antibody. The preparation of such conjugates can be achieved using a variety of known techniques. For example, the methods described by Yoshitake et al, *Eur. J. Biochem.*, 101, 395, 1979, and in U.S. Pat. No. 5,106,732 to Kondo et al, the entire contents of both of which are incorporated herein by reference. As shown in FIG. 3, the detection antibodies of the present disclosure are specific to different analytes (TIMP2 and IGFP7) and each is conjugated to horseradish peroxidase enzyme (detectable label). The HRP enzyme can then be contacted with a substrate, such as a luminogenic substrate that reacts with (e.g., oxidizes) the substrate and provides a detectable signal (e.g., light, luminescence) in each well.

Regardless of the detection antibodies used in the present methods, an amount of each respective detection antibody is provided to each receptacle of the solid phase such that the antigen-binding portion of the detection antibody comes in contact with the corresponding antigen (if present) in portion of sample that has been bound by a corresponding capture antibody.

One of ordinary skill in the art can readily determine the appropriate amount of detection antibody to provide to each receptacle. In specific embodiments, the amount of detection antibody dispensed into each receptacle can be different or the same. Determination of the amount of detection antibody to deposit in each receptacle will depend on various factors, such as the type of sample, the type of analyte of interest, the type and shape of receptacle, the detection method employed and/or the type of detection antibody used.

A detection antibody may be dispensed directly into a receptacle or pre-mixed in a solution that includes a desired concentration of detection antibody and provided as an aliquot of such pre-mixed solution. Methods for diluting a stock solution of antibody are known to those of ordinary skill in the art.

In some embodiments, the amount of detection antibody provided to each receptacle is from about 0.02 µg to about 1.2 µg. In one embodiment, the amount of detection antibody provided to each receptacle is from 0.02 µg to 1.2 µg. In specific embodiments, the amount of detection antibody provided to each receptacle is 0.02 µg, 0.025 µg, 0.03 µg, 0.035 µg, 0.04 µg, 0.045 µg, 0.05 µg, 0.055 µg, 0.06 µg, 0.065 µg, 0.07 µg, 0.075 µg, 0.08 µg, 0.085 µg, 0.09 µg, 0.095 µg, 0.1 µg, 0.15 µg, 0.2 µg, 0.25 µg, 0.3 µg, 0.35 µg, 0.4 µg, 0.45 µg, 0.5 µg, 0.55 µg, 0.6 µg, 0.65 µg, 0.7 µg, 0.75 µg, 0.8 µg, 0.85 µg, 0.9 µg, 0.95 µg, 1.0 µg, 1.05 µg, 1.1 µg, 1.15 µg, 1.2 µg, 1.25 µg or more. In a specific embodiment, the amount of detection antibody provided to each receptacle is 0.075 µg or 1.2 µg.

In other embodiments, the amount of detection antibody provided to a receptacle can be from 1-10 µg/mL, 1-5 µg/mL, 1-4 µg/mL, 1-3 µg/mL, 1-2 µg/mL or less of detection antibody per receptacle. In certain embodiments the amount of detection antibody is from about 0.5 µg/mL to about 2.0 µg/mL. In specific embodiments the amount of detection antibody is 0.5 µg/mL or 2.0 µg/mL per receptacle.

A detection antibody can be administered to a receptacle by any means known to one of ordinary skill in the art. Non-limiting examples of ways to administer a detection antibody include dispensing by, for example, injecting, spraying or pouring the detection antibody to a receptacle. Routine care in the methods of administering a detection antibody such as, the use of sterile techniques or other methods to prevent contamination are understood by those of ordinary skill in the art.

Administration of a detection antibody or a solution comprising a detection antibody can be carried out by an individual or an automated device, such as an automated immunodiagnostic device. Methods for dispensing and contacting a solid phase with a detection antibody can include manually pipetting or placing a desired amount of detection antibody in the receptacle, and/or by way of robotic or automated dispensing mechanisms.

In embodiments where the present methods are carried out, in-whole or in-part, by an automated immunodiagnostic, device, the detection antibody is first provided to a designated reservoir and an aliquot of the detection antibody is subsequently dispensed to a receptacle or multiple receptacles of a solid phase, which has been provided to the automated immunodiagnostic device. Suitable automated immunodiagnostic devices for use in the present methods are known in the art. For example, certain automated immunodiagnostic devices are described in U.S. Pat. Nos. 7,312,084, 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety.

The in specific embodiments the automated immunodiagnostic device is: Ortho Clinical Diagnostics VITROS® ECiQ, Ortho Clinical Diagnostics VITROS® 3600, Ortho Clinical Diagnostics VITROS® 5600, Beckman ACCESS®, Abbott AXSYM®, Roche ELECSYS® or a Dade Behring STRATUS® device.

In one embodiment, the methods of the present disclosure are carried out in one of the following automated immunodiagnostic devices: Ortho Clinical Diagnostics VITROS® ECiQ, Ortho Clinical Diagnostics VITROS® 3600 or Ortho Clinical Diagnostics VITROS® 5600.

Regardless of the type, amount or way in which a detection antibody is provided to a receptacle the detection antibody is incubated in the receptacle. Incubation permits recognition and binding of the antigen-binding portion of the detection antibody to a corresponding antigen (analyte) in the sample. Binding of a detection antibody to an analyte of interest in the sample results in the formation of capture antibody-analyte-detection antibody complexes within the receptacle. The incubation period can be readily determined by one of ordinary skill in the art and can vary based on the various factors, such as the type of sample, the type of antibody, the type of analyte of interest, the type and shape of receptacle, and/or the detection method employed.

Incubation can be for any duration greater than 1 second. In one embodiment, a detection antibody is dispensed into a receptacle and incubated for, at least 1 minute, at least 2 minutes, at least 3 minutes, at least 4 minutes, at least 5 minutes, at least 6 minutes, at least 7 minutes, at least 8 minutes, at least 9 minutes, at least 10 minutes or more. In a specific embodiment, the detection antibody is provided to a receptacle and incubated for at least 5 minutes. In a specific embodiment, the detection antibody is provided to a receptacle and incubated for at least 8 minutes.

In certain embodiments, the detection antibody is provided to a receptacle and incubated for about 1-40 minutes, 1-30 minutes, 1-20 minutes, 1-15 minutes, 1-10 minutes, 1-9 minutes, 1-8 minute, 1-7 minutes, 1-6 minutes, 1-5 minutes, 1-4, minutes, 1-3 minutes, 1-2 minutes or less than 1 minute. In some embodiments, the detection antibody is provided to a receptacle and incubated for 5-10 minutes, 6-10 minutes, 7-10 minutes, 8-10 minutes or 9-10 minutes. In other embodiments, the detection antibody is provided to a receptacle and incubated for 4-9 minutes, 4-8 minutes, 4-7 minutes, 4-6 minutes or 4-5 minutes. In other embodiments, the detection antibody is provided to a receptacle and incubated for 5-9 minutes, 5-8 minutes, 5-7 minutes or 5-6 minutes. In other embodiments, the detection antibody is provided to a receptacle and incubated for 6-9 minutes, 6-8 minutes, or 6-7 minutes. In yet other embodiments, the detection antibody is provided to a receptacle and incubated for 7-9 minutes, or 7-8 minutes.

In certain embodiments, the detection antibody is dispensed as a solution into a receptacle and incubated for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 minutes. In specific embodiment, the detection antibody dispensed into a receptacle and incubated for 4, 5, 6, 7, 8, 9 or 10 minutes. In other embodiments, the detection antibody is incubated in a receptacle for 8 minutes.

In certain embodiments, the sample is premixed with the detection antibody prior to administering the sample and detection antibody mixture to a receptacle. In such embodiments, the sample and detection antibody are mixed and incubated for about 1-40 minutes, 1-30 minutes, 1-20 minutes, 1-15 minutes, 1-10 minutes, 1-8 minutes, 1-5 minutes, 1-4, minutes, 1-3 minutes, 1-2 minutes or less than 1 minute prior to administering the mixture or a portion thereof to a receptacle. In one embodiment, the sample and detection antibody mixture is incubated for 1-10 minutes, inclusive. In another embodiment, the sample and detection antibody mixture is incubated for 1-8 minutes, inclusive. In yet other embodiments, the sample and detection antibody mixture is incubated for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 minutes. The incubation period can be readily determined by one of ordinary skill in the art and can vary based on the various factors. As such, longer or shorter incubation periods are contemplated.

Generation of a detectable signal from the detectable label can be performed using various optical, acoustical, and electrochemical methods well known in the art. Examples of detection modes include fluorescence, radiochemical detection, reflectance, absorbance, amperometry, conductance, impedance, interferometry, ellipsometry and the like.

In some embodiments, the detectable signal is generated by a fluorometer that employs an excitation light source transducer, which is spatially separate from the solid phase, that directs the excitation light to each well being analyzed to produce a detectable wavelength of light in the well, which can be measured by an optical detector.

In yet other embodiments, antibody-based biosensors may also be employed to determine the presence or amount of analyte bound to detection antibodies present in a receptacle.

In one embodiment, the detectable label conjugated to each detection antibody is an enzyme, such as a peroxidase enzyme. In certain embodiments, the detectable label conjugated to each detection antibody is horseradish peroxidase (HRP) or a suitable isozyme thereof. Suitable isozymes of horseradish peroxidase include Type VI and Type IX available, for example from Sigma Chemical. A detectable signal is produced, for example, by providing a substrate, such as a luminogenic substrate, to each well such that the HRP enzyme oxidizes the luminogenic substrate, which then emits a detectable signal (light).

Luminogenic substrates for use with HRP enzyme are known by those of ordinary skill in the art, as are enhances thereof. Non-limiting examples of luminogenic substrates for us in the present example include luminol (i.e., a 2,3-dihydro-1,4-Phthalazinedione) or a substituted luminol and a perborate in an aqueous solvent, as described in U.S. Pat. Nos. 5,846,756 and 5,705,357, the entire contents of each of which are incorporated herein by reference.

In other embodiments, alkaline phosphatase conjugated to the detection antibody and an AMPPD chemiluminescent substrate with Emerald enhancer (Tropix) is used to develop a detectable signal, as described in C. Vigo-Pelfrey et al. *J Neurochem* (1994) 61:1965-1968, the entire contents of which are expressly incorporated herein by reference. As such, the specific combination(s) of enzyme, substrate and enhancer are not intended to be limiting.

In certain embodiments, such as the exemplary embodiment shown in FIG. 3, the luminogenic substrate (e.g., luminol, a derivative thereof and a peracid salt) is provided with an electron-transfer agent (enhancer), such as a substituted acetanilide, to amplify the light signal emitted by the substrate, as well as prolong emission of the signal from the receptacle.

In the present methods, any enhancer can be used which can facilitate electron-transfer from an enzyme (e.g., hydrogen peroxide (derived from perborate)) via peroxidase to luminol. For example, when the reaction between luminol and hydrogen peroxide is brought about by the peroxidase in the presence of a suitable enhancer, the enhancer increases the rate of oxidation by the enzyme. Non-limiting examples of enhancers for use in the present methods include those described in U.S. Pat. No. 4,842,997 and U.S. Pat. No. 5,279,940, the entire contents of each of which are incorporated herein by reference. Suitable enhancers include 4-iodophenol, 4-bromophenol, 4-chlorophenol, 4-phenylphenol, 2-chloro-4-phenylphenol, 6-hydroxybenzothiazole, 4-4$^1$-(2$^1$-methyl)thiazolyl!phenol, 4-2$^1$-(4$^1$-methyl)thiazolyl!phenol, 4-(2'-benzothiazolyl)phenol, 3-(10-phenothiazyl)-n-propylsulphonate and 3-chloro, 4-hydroxyacetanilide.

Incubation of the luminogenic substrate and electron-transfer agent facilitates oxidation of the substrate and amplification of the luminescent signal. Incubation can be for any duration greater than 1 second. The incubation period can be readily determined by one of ordinary skill in the art and can vary based on the various factors. As such, longer or shorter incubation periods are contemplated.

In one embodiment, a luminogenic substrate and electron-transfer agent are dispensed into a receptacle and incubated for, at least 1 minute, at least 2 minutes, at least 3 minutes, at least 4 minutes, at least 5 minutes, at least 6 minutes, at least 7 minutes, at least 8 minutes, at least 9 minutes, at least 10 minutes or more. In a specific embodiment, the luminogenic substrate and electron-transfer agent are provided to a receptacle and incubated for at least 4 minutes. In a specific embodiment, the luminogenic substrate and electron-transfer agent are provided to a receptacle and incubated for at least 5 minutes.

In certain embodiments, the luminogenic substrate and electron-transfer agent are provided to a receptacle and incubated for about 1-20 minutes, 1-15 minutes, 1-10 minutes, 1-9 minutes, 1-8 minute, 1-7 minutes, 1-6 minutes, 1-5 minutes, 1-4, minutes, 1-3 minutes, 1-2 minutes or less than 1 minute. In other embodiments, the detection antibody is provided to a receptacle and incubated for 4-9 minutes, 4-8 minutes, 4-7 minutes, 4-6 minutes or 4-5 minutes. In some embodiments, the luminogenic substrate and electron-transfer agent are provided to a receptacle and incubated for 3-9 minutes, 3-8 minutes, 3-7 minutes, 3-6 minutes or 3-5 minutes. In other embodiments, the luminogenic substrate and electron-transfer agent are provided to a receptacle and incubated for 2-6 minutes, 2-5 minutes, 2-4 minutes or 2-3 minutes. In a specific embodiment the luminogenic substrate and electron-transfer agent are provided to a receptacle and incubated for 4-5 minutes.

In some embodiments, the luminogenic substrate and electron-transfer agent are dispensed into a receptacle and incubated for 1, 2, 3, 4, 5, 6, 7, 8, 9, 10, 11, 12, 13, 14 or 15 minutes. In specific embodiments, the luminogenic substrate and electron-transfer agent are dispensed into a receptacle and incubated for 3, 4, 5, or 6 minutes. In other embodiments, the luminogenic substrate and electron-transfer agent are incubated in each receptacle for 4 minutes. In one embodiment, the luminogenic substrate and electron-transfer agent are incubated in each receptacle for 5 minutes.

Temperature of incubation can be readily determined by one of ordinary skill in the art and can vary based on the various factors. In certain non-limiting examples, the luminogenic substrate and electron-transfer agent are dispensed into a receptacle and incubated at a temperature between 32° C. and 37° C., 33° C. and 37° C., 34° C. and 37° C., 35° C. and 37° C. or 36° C. and 37° C., inclusive. In a specific embodiment, the luminogenic substrate and electron-transfer agent are dispensed into a receptacle and incubated at a temperature of about 37° C. In one embodiment, the luminogenic substrate and electron-transfer agent are dispensed into a receptacle and incubated at a temperature of 37° C.

In one embodiment of the present methods, the luminogenic substrate and electron-transfer agent are dispensed into a receptacle and incubated for about 5 minutes at a temperature of about 37° C. In another embodiment of the present methods, the luminogenic substrate and electron-transfer agent are dispensed into a receptacle and incubated for 4-5 minutes at 37° C.

The present methods can be deployed for the simultaneous or serial detection of two or more different analytes using a single solid phase with high sensitivity and minimal interference from the other analytes. Generally, the signal generated by the detection antibody, either directly or indirectly, after application of the sample to the solid phase can be detected by any means known by one of ordinary skill in the art. Methods for detection, including automated methods, are well known to those having ordinary skill in the art. For example, the signal can be detected visually or obtained by a device (analytical instrument), such as a reflectometer, a fluorometer, or a transmission photometer.

In certain non-limiting examples, robotic instrumentation (i.e., an automated immunodiagnostic device) including, but not limited to, Ortho Clinical Diagnostics VITROS® 3600, Ortho Clinical Diagnostics VITROS® ECiQ device, Ortho Clinical Diagnostics VITROS® 5600, Beckman ACCESS®, Abbott AXSYM®, Roche ELECSYS®, Dade Behring STRATUS® systems are used in conjunction with the present methods to measure a detectable signal. However, any automated immunodiagnostic device capable of detecting the particular signal used in the present methods may be utilized. By way of example only, any fluorometer can be used to detect fluorescent labels; any luminometer can detect a label that emits a wavelength of light; and a reflectometer can be used to detect labels which absorb light.

In certain embodiments, multiple analytes are detected in succession. Here, the detectable signal produced in the first receptacle is measured, then the detectable signal produced by another receptacle is measured, until each receptacle being analyzed has been measured. Detecting the presence of the signal from different receptacles in succession increases efficiency and eliminates the need for multiple, fluorometers, luminometers or reflectometers, which would be required to detect the signal produced by multiple wells at the same time. Further, detection of analytes in succession enables the use of detectable labels that emit a detectable signal having overlapping wavelengths (spectra), or absorption (color).

For example, after each receptacle has been removed from a solid phase a first receptacle is incubated for a predetermined time and pushed to a read station containing for example, a reflectometer, luminometer, electrometer and read. Once the measurement is recorded, the receptacle can be discarded. Next, a second receptacle is passed to the read station and read. The second measurement is recorded and the second receptacle from the solid phase is discarded.

In some embodiments, when a signal is generated and detected (indicating the presence of an analyte in the sample), the signal is then measured and quantified. In specific embodiments the measured amount of signal in each receptacle is quantified to and provided as a single a single value. Any software or methods for combining multiple measurements to provide a single quantified value known to those of ordinary skill in the art can be used in a quantification step of the present methods, such as those set forth, for example, in WO2011073741 A1.

In one non-limiting example, for quantitative measurements, calibration curves are fitted using a modified four- or five-parameter log-logistic software program, e.g., Ortho Clinical Diagnostics, Assay Data Disk (on VITROS® 3600 Immunodiagnostic System, VITROS® 5600 Integrated System) or a magnetic card (on VITROS® ECiQ device). Here, signal levels from a calibrator present in the device used to measure the detectable signal from each receptacle will adjust the master curve provided by the program, and the software determines analyte concentration in each well by applying the signal obtained from each well to the calibration curve.

In certain embodiments, a single value can be provided that quantifies the total amount of all analytes present in the sample. For example, in instances where the present methods are being deployed to detect the presence of two different analytes of interest, the detected amount of the first analyte in the first receptacle is multiplied by the detected amount of second analyte in the second receptacle and the total is then divided by 1000. Hence, the following formula can be used to obtain a single numerical value for the amount of first and second analyte present in a sample: Value=([Analyte 1]×[Analyte 2])/1000. Units=$(ng/mL)^2$/1000.

In other embodiments, the amount of signal measured in each receptacle correlates to the amount of an analyte present in the sample.

In certain embodiments, the detected signal(s) can be compared to that generated after the use of a control sample in the present methods. Such a comparison can facilitate quantification of the amount of analyte detected in a sample. In one embodiment, the amount of signal produced by each receptacle is directly proportional to the concentration of that particular analyte present in the sample. As would be the case in a "sandwich assay".

In another embodiment, the amount of signal produced by each receptacle is inversely proportional to the concentration of that particular analyte of interest in a sample. Such as would be the case in a competitive immunoassay.

In certain embodiments, the method is practiced in an immunoassay. Various specific assay formats are useful in the practice of present methods, and include immunochemical assays, such as enzyme immunoassays, sandwich assays, competitive binding assays, direct binding assay, and others well known in the art.

In a certain embodiment, such as those shown in FIGS. 1-3, the present methods include "sandwich assays" whereby the analyte(s) of interest (e.g., an antigen present in a sample) is complexed with at least a first capture antibody, and a second, detection antibody either simultaneously or in succession. For example, in a specific embodiment a capture antibody is immobilized on the surface of a solid phase. Next, a sample is provided to the solid phase, such that a second (detection) antibody specific to the same analyte of interest binds to a corresponding antigen in the sample to form a capture antibody-analyte-detection antibody complex, i.e., sandwich. When one of the antibodies of the sandwich include a detectable label (e.g., conjugated to a peroxidase, fluorescent dye, or radio-label) or is capable of being so labeled through additional specific binding reactions (such as through an avidin-biotin complex) then the amount of antigen (analyte) present in the sample can be determined.

Other embodiments include competitive binding assays wherein a specific analyte of interest competes with a detection antibody of the analyte and another ligand of the analyte. For example, in a competitive immunoassay format, an antigen in the sample may compete for binding to the detection antibody having a labeled antigen provided as an assay reagent with analytes or antigens provided to the solid phase.

Kits.

In certain aspects of the present disclosure, kits for performing the methods described herein are provided. Suitable kits comprise reagents sufficient for performing a method of the present disclosure, together with instructions for performing the described methods. Additional optional elements that may be provided as part of an assay kit are described herein.

In certain embodiments, reagents for performing the present methods are provided in a kit. Reagents of a kit include one or more of the following, a solid phase, antibodies, buffer solutions, a luminogenic substrate, an electron transfer agent and instructions for performing the methods of the present disclosure.

In some embodiments, a kit includes a solid phase having a plurality of receptacles coated with at least 2 capture antibodies. In specific embodiments, each receptacle of a solid phase provided in a kit has at least two different capture antibodies immobilized thereto, such that each of the at least two different capture antibodies recognize a different antigen or epitope (analyte).

As described herein, a solid phase can include two or more capture antibodies immobilized to each receptacle of the solid phase depending on the number of analytes detected. In certain embodiments, each receptacle of a solid phase has at least 2, at least 3, at least 4, at least 5, at least 6 or more different capture antibodies immobilized thereto. In certain embodiments, each receptacle of a solid phase has 2, 3, 4, 5, 6, 7, 8, 9, 10, or more different capture antibodies immobilized thereto.

In certain embodiments, the capture antibodies immobilized to each receptacle of a solid phase are mouse monoclonal antibodies specific to TIMP2 and IGFBP7. In a specific embodiment, the capture antibody specific to TIMP2 is mouse monoclonal antibody 6E2. 1 and the capture antibody specific to IGFBP7 is mouse monoclonal antibody 1D6.

In other embodiments, the kit includes a solid phase that has at least two capture antibodies immobilized to a surface of a receptacle that are selected from the following, non-limiting list of antibodies: any monoclonal or polyclonal antibody that specifically recognizes tau (e.g., HT7 and AT270 monoclonal antibodies; antibodies recognizing normally and abnormally phosphorylated tau (e.g., Alz50 (Ghanbari et al., 1990), HT7 (Mercken et al., 1992) and AT120 (Vandermeeren et al., 1993)); any antibody recognizing PSA or a binding partner there of (e.g., 2E9, 2H11 and 5A10 as described in U.S. Pat. No. 5,501,983, the entire contents of which is incorporated herein by reference); any antibody that binds Aβ or a portion thereof, such as those described in U.S. Pat. No. 7,700,309, the entire contents of which is incorporated herein by reference; and other antibodies known to those of ordinary skill in the art such as, for example, those disclosed in U.S. Pat. No. 9,174,097, the entire contents of which is incorporated herein by reference.

In certain instances, a kit includes a solid phase composed of a plurality of receptacles as part of a straw, sleeve, a strip, a plate, a slide, or the like. Specifically, the solid phase includes a straw or strip of cups or wells, a multiwell plate, a microwell plate or the like, which can be used in an automated immunodiagnostic devices. In one embodiment, the solid phase provided in a kit includes a plurality of tapered receptacles, such as VITROS® Microwells.

In some embodiments of the present methods, a solid phase provided in a kit includes at least 2 receptacles, at least 10 receptacles, at least 15 receptacles, at least 20 receptacles, at least 25 receptacles or more. In an embodiment, a solid phase is provided that includes a straw or sleeve of at least two VITROS® Microwells. In another embodiment, a solid phase is provided that includes a straw or sleeve of at least 20 VITROS® Microwells. In another embodiment, a solid phase is provided that includes a straw or sleeve of at least 25 VITROS® Microwells.

In certain embodiments the solid phase provided in a kit includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 receptacles. In some embodiments, the solid phase includes 2-100, 2-75, 2-50, 2-25, 2-15, 2-10 or 2-5 receptacles. In one embodiment, the solid phase includes 25 tapered receptacles. In specific embodiments, the solid phase includes 25 receptacles in a straw or sleeve. In a specific embodiment, the solid phase includes 25 VITROS® Microwells in a sealed straw.

In certain embodiments, kits of the present disclosure include more than one solid phase. For example, a kit may include at least 2, 3, 4, 5, 6, 7, 8, 9 or 10 solid phases that each includes at least 2 receptacles. In certain embodiments, a kit includes 2-10, 2-9, 2-8, 2-7, 2-6, 2-5, 2-4 or 2-3 solid phases that include at least 2 receptacles. In one embodiment, a kit includes 3-6, 3-5 or 3-4 solid phases that each includes at least two receptacles. In a specific embodiment, the kit includes 4 solid phases that each includes at least two receptacles.

In one embodiment, a kit of the present disclosure includes four solid phases each containing a straw or sleeve of at least 10 tapered receptacles. In another embodiment, a kit of the present disclosure includes four solid phases each containing a straw or sleeve of at least 20 tapered receptacles. In yet another embodiment, a kit of the present disclosure includes four solid phases each containing a straw or sleeve of 25 tapered receptacles. In one embodiment, a kit of the present disclosure includes four solid phases each containing a straw or sleeve of 25 VITROS® Microwells.

In some embodiments, a kit includes at least two different detection antibodies whereby each of the at least two different detection antibodies recognizes a different analyte of interest. In some embodiments, each of the at least two different detection antibodies include detectable labels that are the same or produce the same detectable signal.

In some embodiments, the detection antibodies are monoclonal antibodies, polyclonal antibodies, fragments thereof or any combination thereof. In specific embodiments, the detection antibodies are all monoclonal antibodies, which each recognize a different analyte of interest. In other embodiments, the detection antibodies are all polyclonal antibodies, which each recognize an analyte of interest. In yet another embodiment, the detection antibodies provided include a combination of monoclonal antibodies and polyclonal antibodies, each of which is specific to a different analyte of interest.

In some embodiments, a kit includes antibodies specific to TIMP2 and IGFP7 analytes. In certain embodiments, the detection antibodies of the present disclosure are monoclonal antibodies specific to TIMP2 and IGFBP7, respectively. In specific embodiments, the detection antibody that is specific to TIMP2 is rabbit monoclonal antibody 40H2-40K3, and the detection antibody that is specific to IGFBP7 is mouse monoclonal antibody 6D2. 1.

In specific embodiments, a kit includes at least two different detection antibodies that each recognize a different analyte of interest and are conjugated to an enzyme, such as horseradish peroxidase (HRP). In other embodiments, a detection antibody provided is selected from the following, non-limiting list of detection antibodies: any monoclonal or polyclonal antibody that specifically recognizes tau (e.g., HT7 and AT270 monoclonal antibodies; antibodies recognizing normally and abnormally phosphorylated tau (e.g., Alz50 (Ghanbari et al., 1990), HT7 (Mercken et al., 1992) and AT120 (Vandermeeren et al., 1993)), any antibody recognizing PSA or a binding partner there of (e.g., 2E9, 2H11 and 5A10 as described in U.S. Pat. No. 5,501,983, the entire contents of which is incorporated herein by reference); any antibody that binds Aβ or a portion thereof, such as those described in U.S. Pat. No. 7,700,309, the entire contents of which is incorporated herein by reference; and other antibodies known to those of ordinary skill in the art such as, for example, those disclosed in U.S. Pat. No. 9,174,097, the entire contents of which is incorporated herein by reference.

In some embodiments, of the present disclosure, a kit includes a luminogenic substrate. Luminogenic substrates for use in the present methods and kits are known by those of ordinary skill in the art, as are enhances thereof. As such, the specific combination(s) of enzyme, substrate and enhancer are not intended to be limiting. In certain embodiments, the luminogenic substrate provided in a kit is luminol or a derivative thereof and a peracid salt. In some embodiments, the kit includes an electron-transfer agent (enhancer), such as a substituted acetanilide that is capable of amplifying a signal produced by the detectable label.

In some embodiments, kits of the present disclosure include a reference solution (calibration solution) that includes a known amount of a particular analyte of interest. In one embodiment, the reference solution can include a known amount or known amounts of at least 2 analytes of interest. In another embodiment, a reference solution can be provided for each corresponding analyte detected by such a kit. The reference solutions can be utilized to form calibration curves, for further quantification of a measured amount of analyte in a sample, as set forth herein.

In certain embodiments, the kits of the present disclosure include one or more solutions or buffers. For example, a kit can contain one or more of the following: phosphate buffer, detection antibody solution (e.g., TIMP2 detection antibody solution, IGFBP7 detection antibody solution), and water (e.g., deionized or sterile).

In general, the instructions provided in kits of the present disclosure will include the methods of the present disclosure. The methods described herein generally include, contacting a sample containing or suspected of containing analytes of interest with a first capture antibody immobilized to a solid phase, which specifically binds to the analyte. The sample is also contacted with a detection antibody that includes a detection agent to form capture antibody-analyte-detection antibody complexes immobilized a solid phase. A signal is then generated by the detection antibody, which is indicative of the presence or amount of complexes formed by the binding of the analytes in the sample to the capture and detection antibodies. The signal is then measured. In certain non-limiting examples, the methods of the present disclosure include chromatographic, mass spectrographic, and protein detection assays. In one such example, robotic instrumentation (i.e., an automated immunodiagnostic device) including, but not limited to, Ortho Clinical Diagnostics ECiQ®, Ortho Clinical Diagnostics VITROS® 3600, Ortho Clinical Diagnostics VITROS® 5600, Beckman ACCESS®, Abbott AXSYM®, Roche ELECSYS®, Dade Behring STRATUS® systems are among the automated immunodiagnostic devices that are capable of being used in conjunction with the present methods. However, any suitable automated immunodiagnostic devices may be utilized to measure a detectable signal.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

Additionally, any reference referred to as being "incorporated herein" is to be understood as being incorporated in its entirety.

EXAMPLES

Example 1: Materials and Methods

Receptacle Formation.

The receptacles (e.g., wells) of the present disclosure are produced by the following 2-day direct antibody coating process. Before coating, the receptacles (e.g., white polystyrene-coated wells) are irradiated to 1 MRad in order to minimize well-to-well differences. A capture antibody coating solution is prepared, containing 30 mM of a phosphate buffer composed of 0.96 mM $K_2HPO_4$ plus 2.04 mM $KH_2PO_4$ in 150 mM NaCl buffer, Sunset Yellow dye (7.5 mg/Kg of solution) at pH 6.3±0.2. TIMP2 capture MAb 6E2.1 and IGFBP7 capture MAb 1D6 murine antibodies are each added to a final concentration of 3 µg/mL. To each well, 200 µL of 3 µg/mL capture antibody coating solution is added. The receptacles are then incubated overnight (e.g., 16 to 32 hours) at 18-22° C. After overnight incubation with capture antibody coating solution, the receptacles are washed twice with a TRIS wash buffer containing 0.1 M Tris/HCl at pH 8.5. After aspiration of the wash buffer, the receptacles are coated with TSSB (0.1 M Tris/HCl at pH 8.5 containing 5% sucrose, 0.45% sodium chloride and 0.1% BSA). All solution is aspirated from each receptacle, and after final aspiration the receptacles are dried. The washes, coat and final aspiration steps are an in-line process with no additional incubation steps. Plates containing the coated receptacles are stored at 18-22° C. in storage containers (e.g., plastic boxes) containing desiccant until used. The receptacles are supplied as 100 coated wells sealed in 4 straws (25 wells per straw). Each receptacle is coated with both TIMP2 and IGFBP7 capture antibodies.

Preparation of Detection Conjugate Reagents.

The TIMP2-HRP and IGFBP7-HRP detection conjugates are prepared from TIMP2 detection MAb40H2-40K3, IGFBP7 detection MAb 6D2.1 and horseradish peroxidase (HRP) using standard conjugation methods known in the art. The TIMP2-HRP conjugate reagent is a 110 mM phosphate buffer solution with pH 6.5, also containing potassium ferricyanide (0.001%), Tween® 20 (0.5%), ProClin™ 950 (0.5%), Anilinonaphthalene-1-Sulfonate (ANS) (0.04%), and Bovine Serum Albumin (BSA) (3.00/%) and 0.0005 g/kg of the TIMP2 antibody conjugate. The IGFBP7-HRP conjugate reagent is a 110 mM phosphate buffer with 100 mM NaCl solution with pH 6.5, also containing potassium ferricyanide (0.001%), Tween® 20 (0.5%), ProClin™ 950 (0.5%), Anilinonaphthalene-1-Sulfonate (ANS) (0.04%/o), and Bovine Serum Albumin (BSA)(3.0%) and 0.002 g/Kg of IGFBP7-HRP conjugate.

Analyte Detection.

To obtain the amount of exemplary analytes present in a sample two assays are run in succession. A first coated receptacle is provided from a solid phase and patient sample is dispensed into the first receptacle, then detection antibody solution reagent including a first detection antibody that binds to a first analyte conjugated to horseradish peroxidase (e.g., TIMP2 HRP conjugate) is dispensed into the first receptacle with the patient sample. Next, a second coated receptacle is provided from a solid phase and patient sample is dispensed into the second receptacle, then detection antibody solution including a second detection antibody that binds to a second analyte conjugated to horseradish peroxidase (e.g., IGFBP7 HRP conjugate) is dispensed into the second receptacle with the patient sample. Both the first well and the second well are incubated at 37° C. for 8 minutes to facilitate the formation of capture antibody-analyte-detection antibody complexes immobilized on the surface of each well. Each receptacle is then washed and aspirated to remove excess detection antibody solution. Signal reagent containing luminogenic substrates (a luminol derivative and a peracid salt) and an a solution containing an electron transfer agent, as described in U.S. Pat. No. 5,846,756, are added to each of the wells. The detection agent (HRP) conjugated to each detection antibody the bound conjugate catalyzes the oxidation of the luminol derivative to producing light, which is emitted from the well. The electron transfer agent present in the signal reagent (a substituted acetanilide) increases the level of light produced by the luminol derivative and prolongs light emission from the well. Light emission is measured for each well. Each receptacle is then positioned in proximity to a luminometer (VITROS® 3600 Immunodiagnostic System or a VITROS® 5600 Integrated System), such that the luminometer can provide a readout of the amount of light emitted from each receptacle.

Due to the efficiency of the present methods, measured amounts of both exemplary analytes, TIMP2 and IGFBP7 are obtained in 16 minutes using an automated immunodiagnostic device (i.e., VITROS® 3600 Immunodiagnostic System, or a VITROS® 5600 Integrated System), as shown in Table 1.

TABLE 1

Exemplary method conditions and time first detected result obtained by multiple automated immunodiagnostic devices

| Automated Device | Analyte | Incubation Time | Time to First Result | Temperature | Reaction Sample Volume |
|---|---|---|---|---|---|
| 3600, 5600 | TIMP2 | 8 minutes | 16 minutes | 37° C. | 35 µL |
| 3600, 5600 | IGFBP7 | 8 minutes | 16 minutes | 37° C. | 20 µL |

Quantification.

The amount of light emitted by each well is directly proportional to the concentration of analyte present in the sample in each receptacle. Depending on the particular method, it may be desirable to obtain a single value derived from the two measured signals. In this example, to obtain a single numerical value, the detected amount of the first analyte in the first well is multiplied by the detected amount of second analyte in the second well and the total is then divided by 1000. For example, the following formula can be used to obtain a single numerical value for the amount of first and second analyte present in a sample. Value=([Analyte 1]×[Analyte 2])/1000. Units=(ng/mL)$^2$/1000.

Example 2. Determining the Amount Two Separate Analytes in a Sample

As shown in FIGS. 1-3, an immunoassay technique is used to detect the presence of two separate analytes (TIMP-2 and IGFBP-7) present in a urine sample using the methods of the present disclosure. Here, a solid phase was provided including wells that have mouse monoclonal antibodies (capture antibodies) specific to analytes, TIMP2 or IGFBP7 immobilized on the surface of each well.

35 µL of urine obtained from a subject (sample) was dispensed in a first well of the solid phase along with a horseradish peroxidase-labeled anti-TIMP2 rabbit monoclonal detection antibody conjugate. During an 8 minute incubation at 37° C., analyte present in the sample binds to the TIMP2 detection antibody to form analyte-detection antibody complexes within the well. These complexes are captured by mouse monoclonal anti-TIMP2 capture antibodies immobilized on the well surface.

20 µL of urine obtained from the subject is dispensed in another well of the solid phase along with a horseradish peroxidase-labeled anti-IGFBP7 mouse monoclonal detection antibody conjugate. The mixture is incubated at 37° C. for 8 minutes to form analyte-detection antibody complexes that are captured by mouse monoclonal anti-IGFBP7 capture antibodies immobilized on the well surface.

After incubation, unbound materials are removed by washing and the remaining solution in each well is aspirated.

The amount of bound horseradish peroxidase-conjugated to each detection antibody is measured by luminescent detection. As shown in FIG. 3, 100 µL of signal reagent containing luminogenic substrate (a luminol derivative and a peracid salt) and 100 µL of an enhancer solution containing an electron transfer agent (a substituted acetanilide) is added to each of the wells and the wells are incubated for 4 to 5 minutes. The horseradish peroxidase conjugated to each detection antibody catalyzes oxidation of the substrate (luminol derivative), producing a detectable wavelength of light (luminescence) in each well. In addition, the electron transfer agent present in the signal reagent mixture increases the level of light produced by the substrate and prolongs light emission. Each of the first and second well emits a light signal having the same wavelength, which are measured in succession by a luminometer.

Measurement of the luminescent signal from each well is carried out by positioning the first well in proximity to the luminometer, such as that present within an automated immunodiagnostic device (e.g., VITROS® 3600 Immunodiagnostic System). The luminometer then reads the luminescent signal for the first well. The second well is then positioned in proximity of the luminometer such that the luminometer can then read the luminescent signal emitted by the second well. In a qualitative assay, a positive or signal can be provided by the luminometer or automated immunodiagnostic device, or not, to show whether analyte is present, or not, in the sample tested.

Example 3: Quantification of Analytes

For quantitative measurements, calibration curves are fitted using a modified four- or five-parameter log-logistic program such as that provided by the manufacturer (Orthoclinical diagnostics, Assay Data Disk (on VITROS® 3600 Immunodiagnostic System; VITROS® 5600 Integrated System) or a magnetic card (on VITROS® ECiQ device). Here, signal levels form a calibrator adjust the master curve provided by the program, and the software determines analyte concentration in each well by applying the luminescent signal obtained from each well to the calibration curve.

The amount of light emitted is directly proportional to the amount of horseradish peroxidase-conjugated detection antibody bound to antigen (analyte) present in the sample. Therefore, the amount of light measured from each well is proportional to the concentration of the analytes present in each sample, i.e., nanograms of analyte per milliliter of urine sample.

The measured amounts of each analyte can be calculated as a single numerical value. Here, the detected amount of the first analyte in the first well is multiplied by the detected amount of second analyte in the second well and the total is then divided by 1000. For example, the following formula can be used to obtain a single numerical value for the amount of first and second analyte present in a sample. Value=([TIMP-2]×[IGFBP-7])/1000. Units=(ng/mL)$^2$/1000.

What is claimed is:

1. A method for detecting analytes comprising:
   providing a solid phase comprising two receptacles, wherein each of said two receptacles comprises a first capture antibody and a second capture antibody affixed thereto, wherein the first capture antibody binds to a first analyte and the second capture antibody binds to a second analyte, and wherein said first analyte and said second analyte are different;
   providing a sample, wherein a portion of the sample is provided to each of the two receptacles;
   providing to the solid phase, a first detection antibody specific to the first analyte and a second detection antibody specific to the second analyte, wherein the portion of said sample in the first receptacle is contacted with said first detection antibody and the portion of said sample in the second receptacle is contacted with said second detection antibody, and wherein said first detection antibody and said second detection antibody produce the same detectable signal; and
   detecting said first analyte and detecting said second analyte in said sample.

2. The method of claim 1, wherein said two receptacles are tapered receptacles.

3. The method of claim 1, further comprising quantifying the amount of analyte detected in each of said two receptacles.

4. The method of claim 3, wherein said quantifying comprises obtaining the detected amount of analyte for each receptacle and providing a single numerical value.

5. The method of claim 1, further comprising dispensing in each of said two receptacles a luminogenic substrate and an electron transfer agent, wherein said luminogenic substrate produces the detectable signal in each of said first receptacle and said second receptacle.

6. The method of claim 5, wherein said detectable signal in each of said first receptacle and said second receptacle is light.

7. The method of claim 6, wherein said detectable signal in each of said first receptacle and said second receptacle is the same wavelength of light.

8. The method of claim 7, wherein said amount of said first analyte in said sample is directly proportional to the amount of light detected in said first receptacle.

9. The method of claim 8, wherein said amount of said second analyte in said sample is directly proportional to the amount of light detected in said second receptacle.

10. The method of claim 5, wherein said luminogenic substrate is oxidized by contacting said detection antibody in the first receptacle or by contacting said detection antibody in the second receptacle.

11. The method of claim 5, wherein said luminogenic substrate comprises a luminol derivative and peracid salt.

12. The method of claim 5, wherein said electron transfer agent is a substituted acetanilide.

13. The method of claim 1, wherein said first detection antibody and said second detection antibody are each conjugated to horseradish peroxidase.

14. The method of claim 1, further comprising incubating the portion of said sample in the first receptacle with the first detection antibody and the portion of said sample in the second receptacle with the second detection antibody for at least five minutes prior to said detecting the amount of each of said first analyte in said sample and said second analyte in said sample.

15. The method of claim 14, wherein said incubation is for a duration of 8 minutes.

16. The method of claim 1, wherein said amount of the first analyte in said sample and said amount of the second analyte in said sample are detected in succession.

17. The method of claim 1, wherein said sample, and said first detection antibody specific to the first analyte and said second detection antibody specific to the second analyte are provided to said solid phase at the same time.

18. The method of claim 1, wherein said sample is a body fluid sample.

19. The method of claim 18, wherein said body fluid sample is urine.

20. The method of claim 1, wherein each of said first capture antibody, said second capture antibody, said first detection antibody and said second detection antibody are monoclonal antibodies.

21. The method of claim 1, wherein said solid phase is configured for use in an automated immunodiagnostic device.

22. The method of claim 21, wherein said portion of said sample is provided to each of the two receptacles by an automated immunodiagnostic device.

23. The method of claim 22, wherein said automated immunodiagnostic device provides said first detection antibody to the portion of the sample in the first receptacle and provides said second detection antibody to the portion of the sample in the second receptacle.

24. The method of claim 23, wherein said detection comprises measurement of an amount of each of said first analyte in said sample and detecting an amount of said second analyte in said sample by said automated immunodiagnostic device.

25. The method of claim 1, wherein said detecting each analyte comprises providing said solid phase to an automated immunodiagnostic device, wherein said automated immunodiagnostic device detects said first analyte in said sample in said first receptacle and detects said second analyte in said sample in said second receptacle.

26. The method of claim 25, wherein said automated immunodiagnostic device comprises a luminometer, and wherein said luminometer detects each of said first analyte said second analyte in succession.

* * * * *